United States Patent [19]

Roe et al.

[11] Patent Number: 5,554,145
[45] Date of Patent: Sep. 10, 1996

[54] ABSORBENT ARTICLE WITH MULTIPLE ZONE STRUCTURAL ELASTIC-LIKE FILM WEB EXTENSIBLE WAIST FEATURE

[75] Inventors: Donald C. Roe, West Chester; David J. K. Goulait; Sheila S. Rodriguez, both of Cincinnati; Edward P. Carlin, Maineville; Kimberly A. Dreier, Cincinnati; Carolyn M. Jasper, Cincinnati; Dean J. Daniels, Cincinnati, all of Ohio

[73] Assignee: The Procter & Gamble Company, Cincinnati, Ohio

[21] Appl. No.: 203,456

[22] Filed: Feb. 28, 1994

[51] Int. Cl.⁶ .................................................. A01F 13/15
[52] U.S. Cl. ........................ 604/385.2; 604/358; 604/373
[58] Field of Search .............................. 604/358, 373, 604/385.1, 385.2, 393–394, 396, 397, 402

[56] References Cited

U.S. PATENT DOCUMENTS

| 235,449 | 12/1880 | Newton . |
| 659,266 | 10/1900 | Stewart . |
| 728,828 | 5/1903 | Arkell . |
| 782,977 | 2/1905 | Madden . |
| 854,763 | 5/1907 | Scriven . |
| 1,507,949 | 9/1924 | Angier . |
| 1,582,842 | 4/1926 | Lorenz . |
| 2,004,088 | 6/1935 | Alsop .................................. 604/397 |
| 2,007,047 | 7/1935 | Gibbs . |
| 2,158,929 | 5/1939 | Dunajeff . |
| 2,177,490 | 10/1939 | Kieffer . |
| 2,257,428 | 9/1941 | Ruegenberg . |
| 2,679,887 | 6/1954 | Doyle et al. . |
| 2,896,692 | 7/1959 | Villoresi . |

(List continued on next page.)

FOREIGN PATENT DOCUMENTS

| 956751 | 10/1974 | Canada . |
| 0307871B1 | 12/1992 | European Pat. Off. . |
| 0532034A3 | 3/1993 | European Pat. Off. . |
| 0567792A1 | 11/1993 | European Pat. Off. . |
| 2432801 | 1/1976 | Germany .............................. 604/373 |
| 4-28364 | 1/1992 | Japan . |
| 4371147 | 12/1992 | Japan ............................... 604/385.2 |
| 4371148 | 12/1992 | Japan ............................... 604/385.2 |
| 6-6818 | 2/1994 | Japan . |
| 2253131 | 9/1992 | United Kingdom .................... 604/385.2 |
| WO93/25171 | 12/1991 | WIPO . |
| WO92/22273 | 12/1992 | WIPO . |
| WO93/09746 | 5/1993 | WIPO . |
| WO93/17648 | 9/1993 | WIPO . |
| WO93/25170 | 12/1993 | WIPO . |

Primary Examiner—John G. Weiss
Assistant Examiner—Mark O. Polutte
Attorney, Agent, or Firm—Steven W. Miller; Kevin C. Johnson; Jacobus C. Rasser

[57] ABSTRACT

Absorbent articles such as disposable diapers, incontinent briefs, diaper holders, training pants, feminine hygiene garments and the like, that have a unique waist feature that improves the dynamic fit as well as the containment characteristics of the absorbent article. Such absorbent articles comprise a chassis assembly preferably comprising a liquid pervious topsheet, a liquid impervious backsheet, and an absorbent core positioned between the topsheet and the backsheet; an extensible back waist feature; and a closure system for maintaining the absorbent article on the wearer. The extensible back waist feature provides an extensible feature that provides a more comfortable and contouring fit by initially conformably fitting the diaper to the wearer and by sustaining this fit. The extensible back waist feature has a hip panel, a central waistband panel, and a pair of side panels. The force/extension characteristics of each panel is designed to provide such improved fit and containment. While each panel of the extensible waist feature may be constructed from a number of extensible materials, the panels preferably comprise a structural elastic-like film web. The structural elastic-like film (SELF) web exhibits an elastic-like behavior in the direction of elongation without the use of added elastic materials. The configuration of the SELF web in each panel has specific characteristics to provide the desired force/extension characteristics of each panel.

7 Claims, 21 Drawing Sheets

U.S. PATENT DOCUMENTS

| | | |
|---|---|---|
| 2,901,951 | 9/1959 | Hochfeld . |
| 2,974,716 | 3/1961 | Fourness . |
| 3,151,947 | 10/1964 | Hastings . |
| 3,236,718 | 2/1966 | Chohn et al. . |
| 3,313,080 | 4/1967 | Gewiss . |
| 3,351,441 | 11/1967 | Gewiss . |
| 3,362,118 | 1/1968 | Brunner . |
| 3,550,423 | 12/1970 | Gewiss . |
| 3,726,408 | 4/1973 | Gewiss . |
| 3,817,827 | 6/1974 | Benz . |
| 3,828,784 | 8/1974 | Zoephel . |
| 3,843,761 | 10/1974 | Bierenbaum et al. . |
| 3,860,003 | 1/1975 | Buell . |
| 3,880,966 | 4/1975 | Zimmerman et al. . |
| 3,894,352 | 7/1975 | Hooker . |
| 3,929,135 | 12/1975 | Thompson . |
| 3,969,473 | 7/1976 | Meek . |
| 3,975,455 | 8/1976 | Falender et al. . |
| 3,992,162 | 11/1976 | Gewiss . |
| 4,024,867 | 5/1977 | Mesek . |
| 4,031,568 | 6/1977 | Huff . |
| 4,036,233 | 7/1977 | Kozak . |
| 4,041,949 | 8/1977 | Kozak . |
| 4,051,854 | 10/1977 | Aaron . |
| 4,082,877 | 4/1978 | Shadle . |
| 4,104,430 | 8/1978 | Fenton . |
| 4,110,391 | 8/1978 | Berzen et al. . |
| 4,153,664 | 5/1979 | Sabee . |
| 4,205,679 | 6/1980 | Repke et al. . |
| 4,321,924 | 3/1982 | Ahr . |
| 4,323,070 | 4/1982 | Ternstrom et al. . |
| 4,324,246 | 4/1982 | Mullane et al. . |
| 4,342,314 | 8/1982 | Radel et al. . |
| 4,425,130 | 1/1984 | DesMarais . |
| 4,463,045 | 7/1984 | Ahr et al. . |
| 4,486,192 | 12/1984 | Sigl . |
| 4,554,121 | 11/1985 | Kramers . |
| 4,568,344 | 2/1986 | Suzuki et al. . |
| 4,576,599 | 3/1986 | Lipner . |
| 4,589,876 | 5/1986 | Van Tilburg . |
| 4,609,518 | 9/1986 | Curro et al. . |
| 4,610,682 | 9/1986 | Kopp . |
| 4,617,241 | 10/1986 | Mueller . |
| 4,640,859 | 2/1987 | Hansen et al. . |
| 4,662,874 | 5/1987 | Korpman . |
| 4,699,620 | 10/1987 | Bernardin . |
| 4,701,174 | 10/1987 | Johnson . |
| 4,704,115 | 11/1987 | Buell . |
| 4,719,261 | 1/1988 | Bunnelle et al. . |
| 4,731,066 | 3/1988 | Korpman . |
| 4,743,241 | 5/1988 | Igaue et al. . |
| 4,756,709 | 7/1988 | Stevens . |
| 4,780,344 | 10/1988 | Hoberman . |
| 4,834,741 | 5/1989 | Sabee . |
| 4,847,134 | 7/1989 | Fahrenkrug et al. . |
| 4,892,536 | 1/1990 | DesMarais et al. . |
| 4,906,243 | 3/1990 | Dravland . |
| 4,935,021 | 6/1990 | Huffman et al. . |
| 4,950,264 | 8/1990 | Osborn . |
| 4,968,313 | 11/1990 | Sabee . |
| 4,977,011 | 12/1990 | Smith . |
| 4,995,873 | 2/1991 | Knight . |
| 5,006,394 | 4/1991 | Baird . |
| 5,008,140 | 4/1991 | Schmertz . |
| 5,028,474 | 7/1991 | Czaplicki . |
| 5,034,078 | 7/1991 | Hodgson, Jr. et al. . |
| 5,151,092 | 9/1992 | Buell et al. . |
| 5,187,817 | 2/1993 | Zolner . |
| 5,196,000 | 3/1993 | Clear et al. . |
| 5,202,173 | 4/1993 | Wu et al. . |
| 5,242,436 | 7/1993 | Weil et al. ............................ 604/385.2 |
| 5,254,111 | 10/1993 | Cancio et al. . |
| 5,296,184 | 3/1994 | Wu et al. . |
| 5,358,500 | 10/1994 | Lavon et al. ......................... 604/385.2 |
| 5,370,634 | 12/1994 | Ando et al. .......................... 604/385.1 |
| 5,383,871 | 1/1995 | Corlin et al. ......................... 604/385.2 |

ABSORBENT ARTICLE WITH MULTIPLE ZONE STRUCTURAL ELASTIC-LIKE FILM WEB EXTENSIBLE WAIST FEATURE

FIELD OF THE INVENTION

The present invention relates to absorbent articles such as diapers, incontinent briefs, training pants, and the like, and more particularly, to absorbent articles having an extensible waist feature providing dynamic fit about the wearer as well as improved containment characteristics of the absorbent article.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art. For example, U.S. Pat. No. Re. 26,152, entitled "Disposable Diaper" issued to Duncan and Baker on Jan. 31, 1967, describes a disposable diaper which has achieved wide acceptance and commercial success. U.S. Pat. No. 3,860,003, entitled "Contractable Side Portions For Disposable Diaper", issued to Buell on Jan. 14, 1975, describes an elasticized leg cuff disposable diaper which has achieved wide acceptance and commercial success.

However, absorbent articles have a tendency to sag or gap away from and to slide/slip down on the body of the wearer during wear. This sagging/gapping and sliding/slipping is caused by the relative motions of the wearer as the wearer breathes, moves and changes positions, by the downward forces generated when the absorbent article is loaded with body exudates, and by the rib-like element of the materials of the absorbent article itself when subjected to such wearer's motions. This sagging/gapping and sliding/slipping of the absorbent article can lead to premature leakage and poor fit of the absorbent article about the wearer in the waist regions and the leg regions of the absorbent article.

In order to more snugly fit absorbent articles about the wearer, certain commercially available absorbent articles have been provided with elastic features. An example of a disposable diaper with elastic side panels is disclosed in U.S. Pat. No. 5,151,092, entitled "Absorbent Article With Dynamic Elastic Waist Feature Having Predisposed Flexural Hinge" issued to Buell, Clear, and Falcone on Sep. 22, 1992. However, elastics are costly and require a certain degree of manipulation and handling during assembly. Further, while elastics do provide a degree of stretch for the absorbent article, the components of the absorbent article to which the elastics are attached are typically not elastic such that the elastics must be prestretched prior to being secured to the absorbent article or the inelastic components must be subjected to mechanical stretching (e.g., ring rolling) to enable the added elastic to be effective. Otherwise, the added elastic is restrained by the inelastic components.

Therefore, it is an object of the present invention to provide a relatively low cost, easy to manufacture, absorbent article having sustained dynamic fit about the wearer during use.

It is a further object of the present invention to provide an absorbent article having a unique extensible waist feature, preferably without the use of elastic, that provides sustained dynamic fit and improved resistance to leakage during use due to the conformability of the materials forming the waist feature by virtue of their readily extensible nature.

It is a still further object of the present invention to provide an extensible waist feature on an absorbent article that exhibits an "elastic-like" behavior in the direction of applied force or elongation without the use of additional elastic material.

It is an even further object of the present invention to provide an extensible back waist feature on an absorbent article that enhances fit and containment by providing multiple zones or panels having different force/extension properties to better distribute the forces encountered by the back waist feature during use and provide the necessary stretch and extension characteristics in those zones.

These and other objects of the present invention will be more readily apparent when considered in reference to the following description and when taken in conjunction with the accompanying drawings.

SUMMARY OF THE INVENTION

The present invention provides absorbent articles such as disposable diapers, incontinent briefs, diaper holders, training pants, feminine hygiene garments and the like, that have an extensible back waist feature that improves the dynamic fit as well as the containment characteristics of the absorbent article. Such absorbent articles comprise a chassis assembly preferably comprising a liquid pervious topsheet, a liquid impervious backsheet, and an absorbent core positioned between the topsheet and the backsheet; an extensible back waist feature having multiple panels or zones; and a closure system for maintaining the absorbent article on the wearer.

In a preferred embodiment of the present invention, the absorbent article has a T-shape comprising a chassis assembly and a extensible back waist feature disposed in the back waist region. The extensible back waist feature provides an extensible member that provides a more comfortable and contouring fit by initially conformably fitting the diaper to the wearer and by sustaining this fit. The extensible back waist feature further develops and maintains wearing forces (tensions) that enhance the tensions developed and maintained by the closure system. The extensible back waist feature further provides more effective application of the diaper. The extensible back waist feature has a central waistband panel, a pair of side panels, and a hip panel. Each of the panels are designed to provide different force and extension properties to optimize the fit of the diaper. While each panel of the extensible back waist feature may be constructed from a number of extensible materials, they preferably each comprise a structural elastic-like film (SELF) web since a SELF web allows the force/extension characteristics to be specifically designed for each panel and with a minimum amount of materials (no conventional elastic materials need to be used).

A structural elastic-like film (SELF) web exhibits an elastic-like behavior in the direction of elongation without the use of added elastic materials. SELF webs exhibit at least two significantly different stages of controlled resistive force to elongation along at least one predetermined axis when subjected to an applied elongation in a direction parallel to the predetermined axis. SELF webs include a strainable network having at least two contiguous, distinct, and dissimilar regions. One of the regions is configured so that it will exhibit resistive forces in response to the applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more rib-like elements which extend beyond the plane of the other region. SELF webs exhibit first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, training pants, feminine hygiene garments, and the like.

Figure 1:
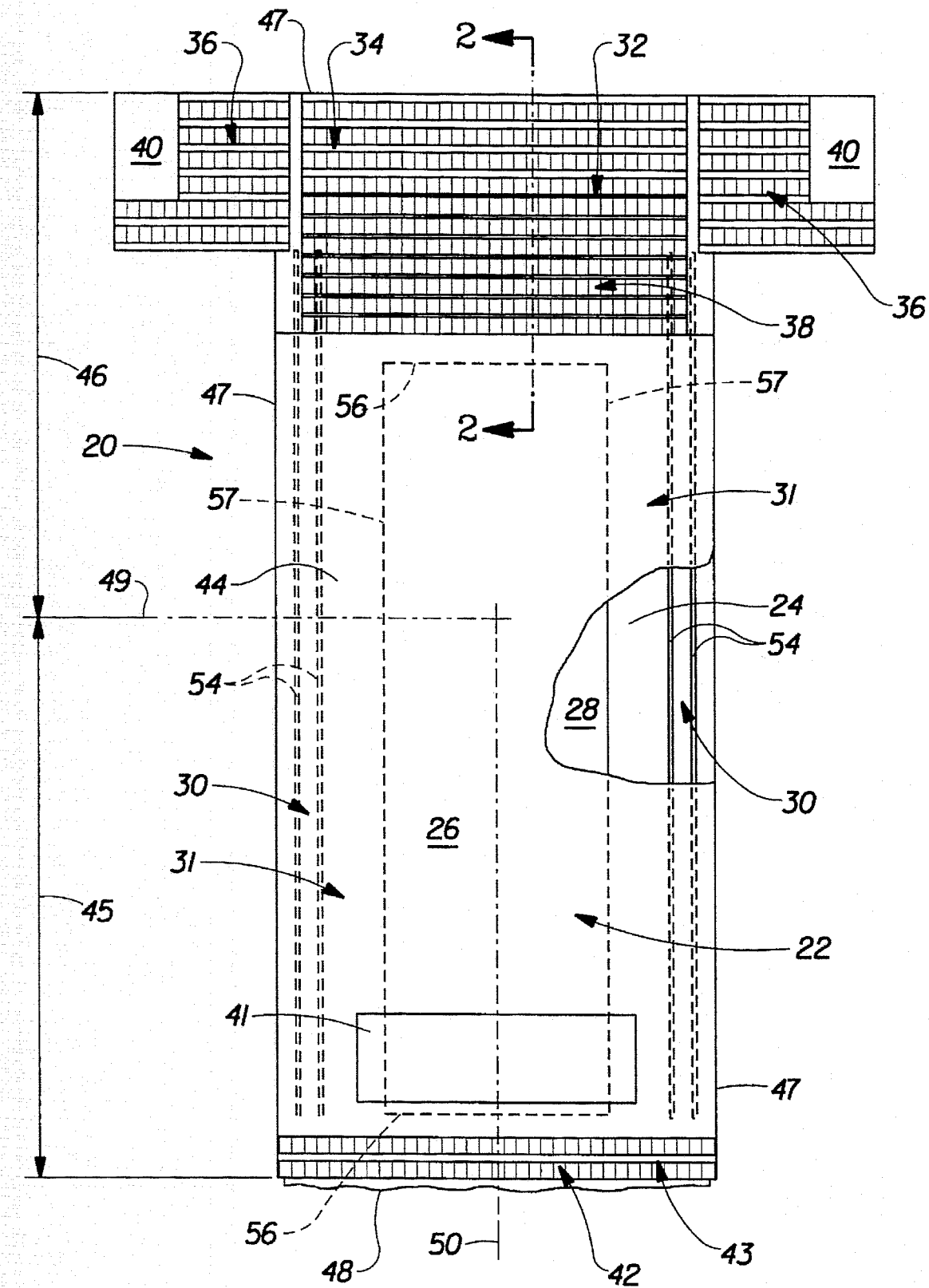
FIG. 1 is a plan view of a disposable diaper embodiment of the present invention having portions cut-away to reveal underlying structure, the outer surface of the diaper facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces away from the wearer, the outer surface, facing the viewer. As shown in FIG. 1, the diaper 20 has a generally "T-shape" and comprises a chassis assembly 22 preferably comprising a liquid pervious topsheet 24, a liquid impervious backsheet 26 joined with the topsheet 24, an absorbent core 28 positioned between the topsheet 24 and the backsheet 26; extensible leg cuffs 30 each comprising a leg flap panel 31 and one or more elastic members, elastic strands 54, operatively joined with the leg flap panel 31; an extensible back waist feature 32 comprising a central waistband panel 34, a pair of side panels 36, and a hip panel 38; a closure system for fastening the diaper on the wearer preferably comprising at least a pair of tape tabs 40 and a landing member preferably comprising a reinforcing strip 41; and an extensible front waist feature 42 comprising a front waist panel 43.

Figure 1A:
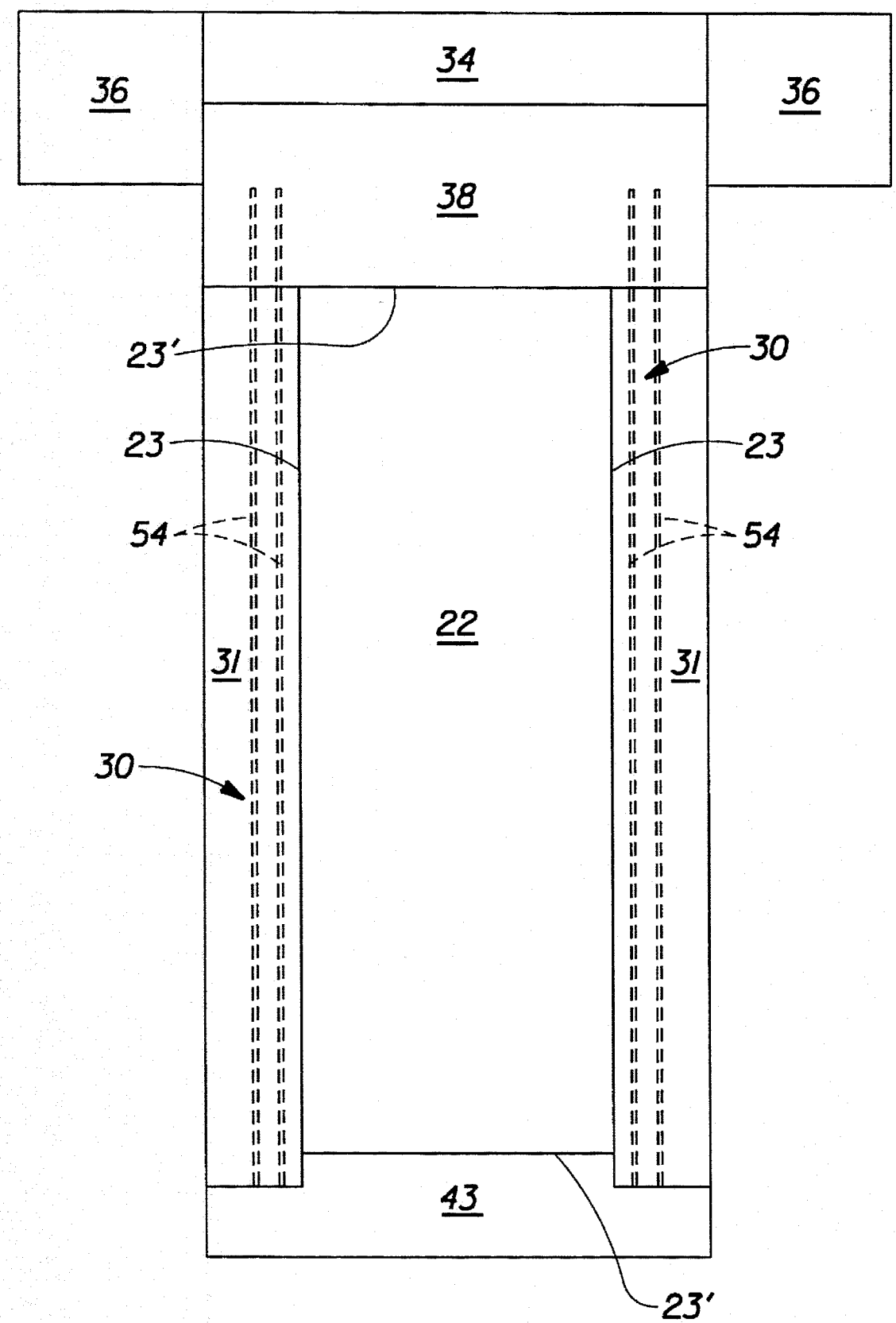
FIG. 1A is a simplified plan view of the disposable diaper embodiment of FIG. 1 depicting the various panels of the diaper.

FIG. 1A shows a simplified plan view of the disposable diaper of FIG. 1 depicting the various panels of the diaper 20 and their positioning with respect to each other. The diaper 20 comprises a chassis assembly or chassis panel 22, a pair of leg flap panels 31, a front waist panel 43, a hip panel 38, a central waistband panel 34, and a pair of side panels 36. The chassis panel or chassis assembly 22 is the main portion of the diaper from which the other panels emanate. The absorbent core is generally positioned within the chassis panel although it may extend into other panels or zones of the diaper. A leg flap panel 31 extends generally laterally outwardly from and along each longitudinal edge 23 of the chassis panel 22. The leg flap panel 31 forms at least a portion of the leg cuff 30. As shown in FIG. 1A, the elastic strands 54 are operatively joined to the leg flap panel 31 to form an extensible leg cuff 30. The front waist panel 43 extends generally longitudinally outwardly from and along the lateral edge 23' of the chassis panel 22 and preferably each leg flap panel 31 in the front waist region. The front waist panel 43 generally forms the extensible front waist feature of the diaper. The hip panel 38 extends generally longitudinally outwardly from and along the lateral edge 23' of the chassis panel 22 and preferably each leg flap panel 31 in the back waist region. The hip panel 38 forms a portion of the extensible back waist feature. The central waistband panel 34 extends generally longitudinally outwardly from and along the hip panel 38. The central waistband panel 34 also forms a portion of the extensible back waist feature. The side panels 36 each extend generally laterally outwardly from and along the central waistband panel 34 and at least a portion of the hip panel 38. The side panels 36 also form a portion of the back extensible waist feature.

As discussed hereinafter, each of the panels may be a separate member joined to the overall diaper structure or may be unitary with the diaper in that they comprise an extension of other elements of the diaper such as the topsheet, the backsheet, or both. In the embodiment shown in FIG. 1, all of the panels except for the side panels 36 comprise an extension of the topsheet 24 and the backsheet 26. The side panels 36 comprise a separate member joined to the central waistband panel 34 and at least a portion of the hip panel 38. Further, any or all of the panels may be extensible. The chassis panel 22 is typically not extensible in order to maintain the integrity of the absorbent core 28 during use, although it may be rendered extensible such as by being formed as a structural elastic-like film (SELF) web as described herein. Preferably, the extensible panels comprise a SELF web. The use of a SELF web allows the force/extension properties of each of the panels to be specifically designed to maximize the fit and containment of the diaper with a minimum amount of materials (no conventional elastic materials are needed).

The diaper 20 of FIG. 1 has an inner surface (not shown), an outer surface 44 (facing the viewer in FIG. 1) opposed to the inner surface, a front waist region 45, a back waist region 46 opposed to the front waist region 45, and a periphery which is defined by the outer edges of the diaper 20 in which the longitudinal edges are designated 47 and the end edges are designated 48. (While the skilled artisan will recognize that a diaper is usually described in terms of having a pair of waist regions and a crotch region between the waist regions; in this application, for simplicity of terminology, the diaper 20 is described as having only waist regions, each of the waist regions including a portion of the diaper which would typically be designated as part of the crotch region). The inner surface of the diaper 20 comprises that portion of the diaper 20 which is positioned adjacent to the wearer's body during use (i.e., the inner surface generally is formed by at least a portion of the topsheet 24 and other components joined to the topsheet 24). The outer surface 44 comprises that portion of the diaper 20 which is positioned away from the wearer's body (i.e., the outer surface 44 generally is formed by at least a portion of the backsheet 26 and other components joined to the backsheet 26). The front waist region 45 and the back waist region 46 extend, respectively, from the end edges 48 of the periphery to the lateral centerline 49 of the diaper 20. (The lateral direction (x direction or width) is defined as the direction parallel to the lateral centerline 49 of the diaper 20; the longitudinal direction (y direction or length) being defined as the direction parallel to the longitudinal centerline 50; and the axial direction (Z direction or thickness) being defined as the direction extending through the thickness of the diaper 20.)

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form certain of the panels and portions of the periphery of the diaper. The periphery defines the outer perimeter or, in other words, the edges of the diaper 20. The periphery comprises the longitudinal edges 47 and the end edges 48.

Figure 2:
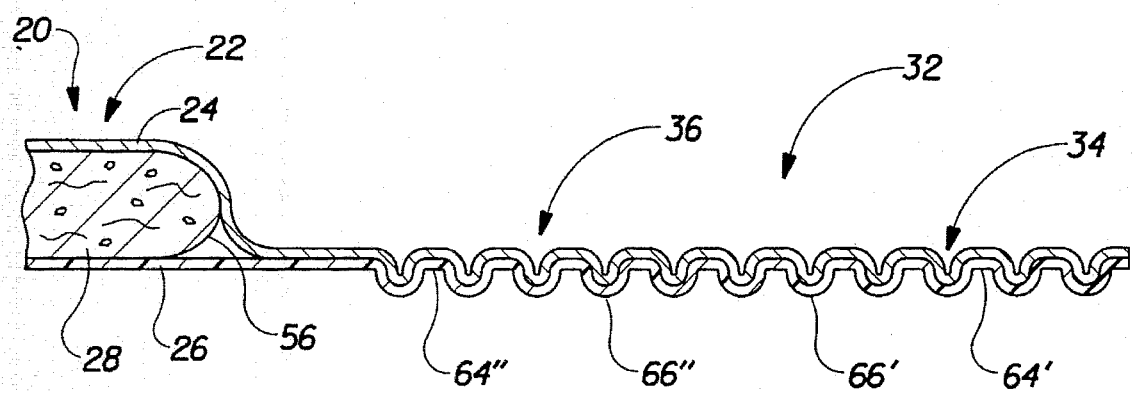
FIG. 2 is a cross-sectional view of the disposable diaper embodiment of FIG. 1 taken through Line 2—2 in FIG. 1.

FIG. 2 is a cross-sectional view of the diaper embodiment of FIG. 1 of the present invention taken through line 2—2 of FIG. 1. FIG. 2 shows the chassis assembly 22 comprising a portion of the topsheet 24, a portion of the backsheet 26, and the absorbent core 28 positioned between the topsheet 24 and the backsheet 26. In the embodiment shown in FIG. 2, the hip panel 38 is joined to and extends longitudinally outwardly from the chassis assembly 22, preferably from the waist edge 56 of the absorbent core 28. The hip panel 38 is unitary with the chassis assembly 22 and comprises a structural elastic-like film (SELF) web comprising the portion of the topsheet and the backsheet extending longitudinally beyond the waist edge. Thus, the extensibility of the hip panel is achieved without the use of a separate elastic material operatively joined to the topsheet and the backsheet. The central waistband panel 34 is joined to and extends longitudinally outwardly from the hip panel 38. The central waistband panel is unitary with the hip panel, and thus the chassis assembly in this embodiment, and comprises a SELF web comprising the portion of the topsheet and the backsheet. The bands 64' of the central waistband panel SELF web are preferably wider (longitudinal dimension) than the bands 64" of the hip panel SELF web with the pleats 66' of the waistband panel SELF web being preferably wider than the pleats 66" of the hip panel SELF web. Thus, the extension forces of the central waistband panel SELF web are higher than the extension forces of the hip panel SELF web.

The chassis assembly 22 (chassis panel) of the diaper 20 is shown in FIGS. 1 and 1A as comprising the main body (chassis) of the diaper 20. The chassis assembly 22 comprises at least an absorbent core 28, preferably an outer covering layer comprising the topsheet 24 and the backsheet 26. Thus, the chassis assembly 22 comprises the main structure of the diaper with other features added to form the composite diaper structure. An exemplary example of a chassis assembly of the present invention is described in U.S. Pat. No. 3,860,003 issued to Kenneth B. Buell on Jan. 14, 1975, which patent is incorporated herein by reference.

The absorbent core 28 may be any absorbent means which is capable of absorbing and retaining liquids such as urine and other certain body exudates. The absorbent core 28 has a garment surface, a body surface, side edges 57, and waist edges 56. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, crosslinked cellulose fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults. FIG. 1 shows a preferred embodiment of the diaper 20 having a rectangular-shape absorbent core.

An absorbent structure useful as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; U.S. Pat. No. 4,888,231 entitled "Absorbent Core Having A Dusting Layer" issued to Angstadt on Dec. 19, 1989; U.S. Pat. No. 5,147,345 entitled "High Efficiency Absorbent Articles For Incontinence Management", issued to Young, LaVon & Taylor on Sep. 15, 1992; U.S. Pat. No. 5,102,597 entitled "Porous, Absorbent, Polymeric Macrostructures and Methods Of Making the Same", issued to Roe, Lahrman and Berg on Apr. 7, 1992; and U.S. Pat. No. 4,834,735, entitled "High Density Absorbent Members Having Lower Density and Lower Basis Weight Acquisition Zones", issued to Alemany and Berg on May 30, 1989; also describe absorbent structures that are useful in the present invention. The absorbent core 28 is preferably the dual-layer absorbent structure described in U.S. Pat. No. 5,234,423 entitled "Absorbent Article With Elastic Waist Feature and Enhanced Absorbency", issued to Alemany and Clear on Aug. 10, 1993. Each of these patents are incorporated herein by reference.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, heat/pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). The backsheet preferably comprises a polyethylene blend film of about 0.025 mm (1.0 mil) as is manufactured by Tredegar Corporation of Terre Haute, Ind. and marketed as P8863.

The topsheet 24 is positioned adjacent the body surface of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to an intermediate member(s) which in turn is affixed to the other element. In a preferred embodiment of the present invention, the topsheet 24 and the backsheet 26 are joined directly to each other in the diaper periphery and are indirectly joined together by directly joining them to the absorbent core 28 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids which have passed through the topsheet and are contained in the absorbent core 28 (i.e., to prevent rewet). If the topsheet is made of a hydrophobic material, at least the upper surface thereof is treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the material with the surfactant and immersing the material in the surfactant. A more detailed discussion of such a treatment and hydrophilicity is contained in U.S. Pat. No. 4,988,344 entitled "Absorbent Articles With Multiple Layer Absorbent Layers" issued to Reising, et al. on Jan. 29, 1991.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 inches). Preferably, the topsheet has a basis weight from about 18 to about 25 grams per square meter. A suitable topsheet is manufactured by Veratec, Inc., a Division of International Paper Company, of Walpole, Mass. under the designation P-8.

The diaper 20 preferably further comprises extensible leg cuffs 30 for providing improved containment of liquids and other body exudates. Each extensible leg cuff 30 may comprise several different embodiments for reducing the leakage of body exudates in the leg regions. (The leg cuff can be and is sometimes also referred to as leg bands, leg flaps, barrier cuffs, or elastic cuffs.) U.S. Pat. No. 3,860,003 entitled "Contractable Side Portions For a Disposable Diaper" issued to Buell on Jan. 14, 1975, describes a disposable diaper which provides a contractible leg opening having a leg flap and one or more elastic members to provide an elasticized leg cuff (gasketing cuff). U.S. Pat. No. 4,909,803 entitled "Disposable Absorbent Article Having Elasticized Flaps" issued to Aziz & Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. U.S. Pat. No. 5,032,120 entitled "Disposable Absorbent Article Having Improved Leg Cuffs" issued to Freeland & Allen on Jul. 16, 1991, discloses an absorbent article having leg cuffs having a relatively low ultimate contact force at relatively high elongations accomplished, for example, by low contact force differential material. U.S. Pat. No. 5,087,255 entitled "Absorbent Article Having Inflected Barrier Cuffs" issued to Sims on Feb. 11, 1992, discloses an absorbent article having inflected barrier cuffs with the distal edge positioned outboard of the proximal edge in one waist region and inboard in the other to provide better fit about the hips/buttocks. Each of these patents are incorporated herein by reference. While each extensible leg cuff 30 may be configured so as to be similar to any of the leg bands, leg flaps, barrier cuffs, or elastic cuffs described above, as shown in FIG. 1, each extensible leg cuff 30 comprises the leg flap panel 31 extending laterally outwardly from the chassis panel 22, the side edge 57 of the absorbent core 28, and one or more elastic members, elastic strands 54, operatively joined with the leg flap panel 31, such as is described in the above-referenced U.S. Pat. No. 3,860,003.

The diaper 20 further comprises extensible waist features that provide improved fit and containment. The extensible waist features at least extend longitudinally outwardly from the chassis assembly, preferably a respective waist edge of the absorbent core 28, and generally form at least a portion of the end edge of the diaper 20. Thus, in the embodiment shown in FIG. 1, the extensible back waist feature 32 comprises that portion of the diaper 20 extending from the waist edge 56 of the absorbent core 28 in the back waist region 46 to the end edge 48 of the diaper 20. While a disposable diaper of the present invention is constructed with an extensible waist feature disposed in each waist region (an extensible back waist feature 32 and an extensible front waist feature 42), the discussion will focus on diapers having different configurations for each extensible waist feature. At a minimum, it is preferred that the diaper at least have one of the extensible waist features constructed according to the present invention, more preferably at least the back extensible waist feature 32. The waist features can be constructed as a separate element joined to the chassis assembly 22 or as an extension of other elements of the diaper (i.e., unitary). The waist features will be described with respect to preferred embodiments in which certain portions or panels comprise an extension of other elements of the diaper such as the backsheet 26, the topsheet 24, or both, and other portions or panels comprise a separate element joined to other portions or panels of the waist feature or other panels of the diaper.

The extensible back waist feature 32 provides an extensible member that provides a more comfortable and contouring fit by initially conformably fitting the diaper to the wearer and sustaining this fit throughout the time of wear well past when the diaper has been loaded with exudates since the extensible back waist feature allows the diaper to expand and, preferably, to contract. Further, the extensible back waist feature develops and maintains wearing forces (tensions) that enhance the tensions developed and maintained by the closure system to maintain the diaper on the wearer and that enhance the fit of the diaper about the waist of the wearer. The extensible back waist feature further provides more effective application of the diaper since even if the diaperer pulls one side (side panel 36) of the extensible back waist feature farther than the other during application (asymmetrically), the diaper will "self-adjust" during wear.

As shown in FIG. 1, the extensible back waist feature 32 comprises a central waistband panel 34; a pair of side panels 36; and a hip panel 38. In the embodiment shown in FIG. 1, the hip panel 38 is disposed longitudinally outwardly from the chassis assembly 22 (the chassis panel), preferably from the waist edge 56 of the absorbent core 28, in the middle zone of the back waist region 46; the central waistband panel 34 is disposed longitudinally outwardly from the hip panel 38; and the side panels 36 are each disposed laterally outwardly from the central waistband panel 34 and at least a portion of the hip panel 38. As discussed hereinafter, the particular positioning of each panel of the back waist feature is important to the overall functioning of the back waist feature. The term "panel" is used herein to denote an area or element of the waist feature or diaper. (While a panel is typically a distinct area or element, a panel may overlap somewhat with an adjacent panel.)

Each of the panels of the back waist feature 32 is extensible so as to dynamically fit and conform to the wearer so as to provide such improved fit and containment. The force/extension properties or characteristics (e.g., extension forces, available stretch (extension), and contractive force(s)) of each of the panels is specifically designed so as to dynamically expand and move with the movements of the body of the wearer adjacent that panel to enhance fit and containment. As discussed hereinafter, since each panel preferably comprises a SELF web as disclosed hereinafter and has a specific and different function, the configuration of and materials comprising the SELF web of each panel are specially selected to provide the different force and extension requirements of each panel, thus enhancing the functioning of diaper.

Figure 3:
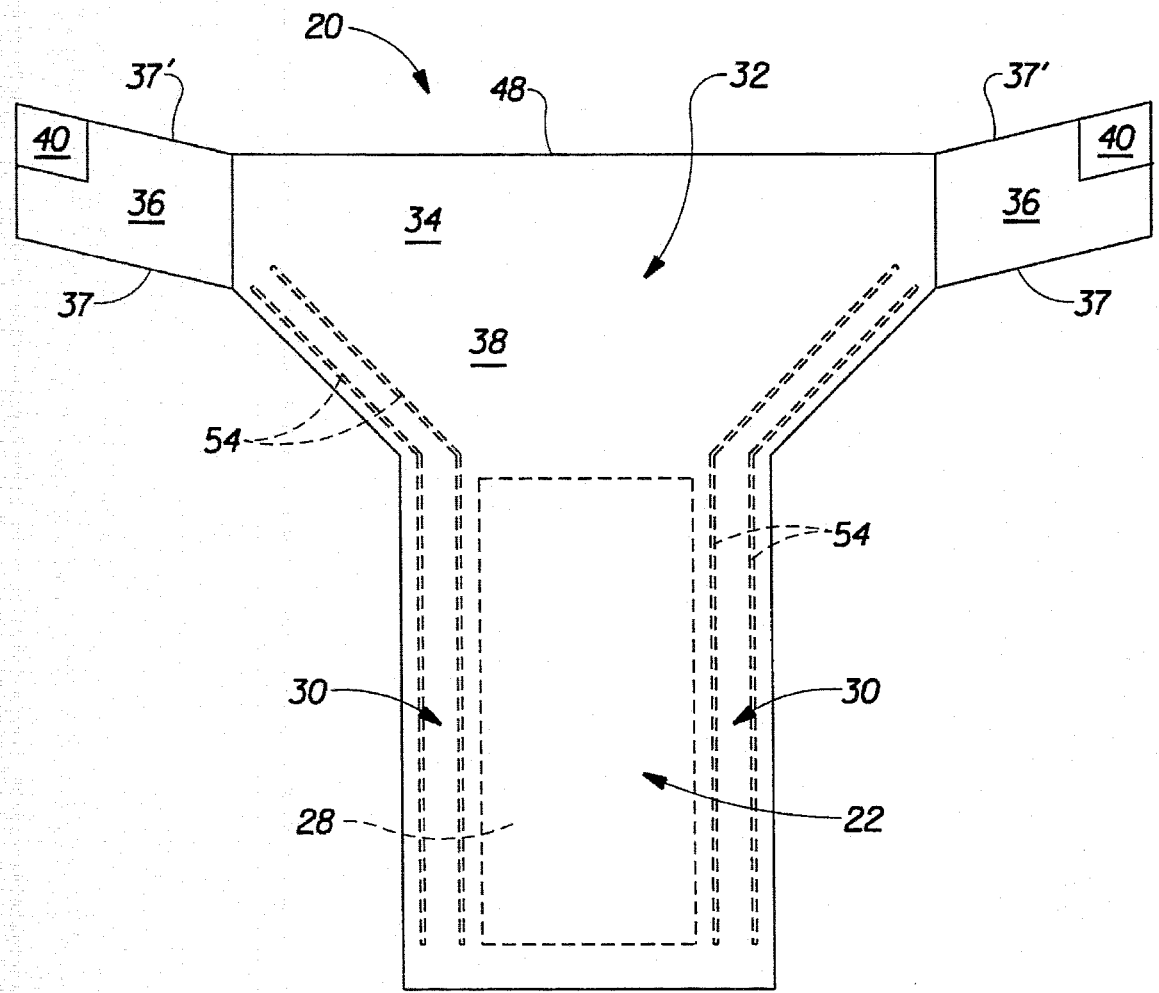
FIG. 3 is a plan view of the disposable diaper embodiment of FIG. 1 in its stretched condition with forces applied to the side panels.

The hip panel 38 is joined to the chassis assembly 22 and is disposed longitudinally between the central waistband panel 34 and the lateral centerline 49, preferably the waist edge 56 of the absorbent core 28 as is shown in FIG. 1, and laterally between the side panels 36. The hip panel 38 is extensible in a direction having a vector component in the lateral direction, preferably in the lateral direction, to provide a more comfortable and contouring fit about the hips and buttocks of the wearer by initially conformably fitting the diaper to the hips/buttocks and sustaining this fit throughout the time of wear since the hip panels allow portions of the diaper to expand with the body and return to its original configuration as the body moves. This additional extensibility in the middle/back of the diaper allows the diaper to better wrap around the wearer's hips and buttocks. As a result, the diaper fits better to the body and reduces sagging, gapping and slippage. The hip panel is designed to have lower extension forces than the central waistband panel, and preferably the side panels, with higher extension capability, available stretch. This enables the diaper to fit wider at the hips than in the central waistband panel, thus reducing the amount of material that is needed to construct the diaper to provide adequate fit and coverage. Preferably, the extension force of the central waistband panel is at least about 2 times, more preferably between 2 to 20 times, most preferably between 5 to 10 times, greater than the extension force of the hip panel. (The extension force of the hip panel should be as low as possible.) In a preferred embodiment, the extension force of the hip panel is less than about 10 g/cm, preferably less than about 5 g/cm, at 50% extension. The hip panel 38, as shown in FIG. 3, thus flairs out after the diaper is applied thereby directing the forces generated in the side panels 36 to transfer to the central waistband panel 34. The hip panel 38 also couples the elastic strands 54 with the waist closure.

The hip panel 38 may take on a number of different sizes and shapes. For example, the hip panel may have a trapezoidal, arcuate, or complex shape. As shown in FIG. 1A, the hip panel 38 preferably has a rectangular shape to minimize material and processing costs. The size of the hip panel may also widely vary, depending upon its available stretch, so long as it provides fit and containment at the hips. In a preferred embodiment of a large (8 kg to 14 kg) baby diaper, the hip panel may, for example, have a size typically about 65 mm long (longitudinal direction) and about 180 mm wide (lateral direction).

The hip panel 38 is extensible in at least one direction, preferably in a direction having a vector component in the lateral direction, more preferably in the lateral direction, to provide better fit by providing extension that follows the hips/buttocks. It should be noted, however, that the hip panel may be extensible in any other direction or in more than one direction. In addition, the hip panel may have one or more discrete zones of extensibility. For example, in one embodiment, the hip panel may have a pair of extensible zones, each positioned laterally outwardly from a central nonextensible zone or panel. In the embodiment shown in FIGS. 1 and 4, the central zone is extensible while the lateral zones are nonextensible. Alternatively, the entire hip panel is extensible to provide the desired functions as described herein.

The hip panel 38 may be constructed in a number of configurations. For example, the hip panel can be constructed of any of the various elastomeric materials or elastomeric laminates as are known in the art. An exemplary elastomeric material is a zero strain stretch laminate such as described in above-referenced U.S. Pat. No. 5,151,092 (Buell, et al.). In an especially preferred embodiment, the hip panel comprises a SELF web as described hereinafter.

The hip panel 38 may comprise a separate element affixed to the chassis panel 22 and the side panels 36 and/or central waistband panel 34 or can be constructed as an extension of other elements of the back waist feature or the diaper such as the backsheet 26 or the topsheet 24, preferably both the topsheet and the backsheet. In the embodiment of the present invention shown in FIG. 1, the hip panel 38 comprises a portion of the topsheet 24 and a portion of the backsheet 26 formed into a SELF web as described hereinafter.

The central waistband panel 34 is the primary component of the extensible back waist feature 32 that provides waist fit and appearance. (The central waistband panel can also be called the waistband or waist panel of the back waist feature.) The central waistband panel 34 is joined to the hip panel 38 and is disposed longitudinally outwardly from the hip panel 38 and laterally inwardly of the side panels 36 so as to fit in the upper back or lumbar zone of the wearer. The central waistband panel 34 is positioned toward the end edge 48 of the diaper 20 to generally define the "central upper segment" of the back waist feature, and preferably, such as is shown in FIG. 1, forms at least a portion of the end edge 48 of the diaper 20. Thus, the central waistband panel 34 provides a member that maintains a defined area coverage, contacts the wearer in the upper back or lumbar zone to snugly fit the wearer, and is extensible, preferably in a direction having a vector component in the lateral direction, more preferably in the lateral direction, so as to dynamically move, fit, and conform to the wearer. The extension forces of the central waistband panel need to be high, generally higher than the hip panel and, preferably, higher than the side panels, in order to support the diaper without sagging, particularly after loading. (The extension force of the central waistband panel is preferably from about 1 to 2 about times as great as the extension force of the side panels). The extension forces are typically between about 10 g/cm to 30 g/cm, preferably between about 15 g/cm and 20 g/cm, at 50% extension. The higher extension forces of the central waistband panel transfer the majority of forces generated in the fitting of the diaper in the side panels to the waist and upper hip regions of the wearer. This enables the diaper to fit higher on the wearer and to allow the tensional forces (a primary line of tension) to be directed about the waist of the wearer, typically downward toward the abdominal crease of the wearer, so as to provide a continuous primary line of tension to hold the diaper on the wearer. This higher fit and continuous line of tension maintains the sustained fit of the diaper. This higher fit also reduces skin marking at the legs and thighs of the wearer.

The central waistband panel 34 may have a number of different sizes and shapes. For example, the central waistband panel may have an arcuate shape so that forces transmitted through the central waistband panel are along a line or zone disposed at an angle to the body of the wearer to fit the diaper into the lumbar curve of the back and to allow the tensional forces (the primary line of tension) to be directed downward toward the abdominal crease of the wearer so as to provide a continuous primary line of tension. Examples of complex shapes useful for the shape of the central waistband panel and the back waist feature are disclosed in U.S. patent application Ser. No. 08/044,562 entitled "Fitted Belt For Absorbent Garment" filed by New, et al. on Apr. 7, 1993, and U.S. patent application Ser. No. 08/072,300 entitled "Absorbent Articles Providing Sustained Dynamic Fit" filed by LaVon, et al. on Jun. 3, 1993; which are incorporated herein by reference. In a preferred embodiment such as is shown in FIG. 1A, the central waistband panel 34 has a rectangular shape. The lateral width of the central waistband panel is typically greater than its longitudinal length. For a typical "large" (8 kg to 14 kg) baby diaper, the central waistband panel may, for example, have a size of about 180 mm in the lateral direction by about 30 mm in the longitudinal direction.

The central waistband panel 34 may be constructed in a number of configurations and from a number of different materials. For example, the central waistband panel may be elasticized by operatively joining an elastic member thereto such as the elasticized waistbands known in the art and as are disclosed in U.S. Pat. No. 4,515,595 issued to Kievit, et al. on May 7, 1985; and U.S. Pat. No. 5,151,092 issued to Buell, et al. on Sep. 29, 1992; each of which are incorporated herein by reference. Thus, the central waistband panel may be a stretch laminate such as a zero strain stretch laminate as is described in U.S. Pat. No. 5,151,092 (Buell, et al.). In a preferred embodiment of the present invention, the central waistband panel comprises a SELF web as described hereinafter.

The central waistband panel 34 may comprise a separate element affixed to the side panels 36 and/or the hip panel 38 or can be constructed as an extension of other elements of the back waist feature or the diaper such as the backsheet 26 or the topsheet 24, preferably both the topsheet and the backsheet. In the embodiment of the present invention shown in FIG. 1, the central waistband panel 34 comprises a portion of the topsheet 24 and a portion of the backsheet 26 formed into a SELF web as described hereinafter.

Figure 4:
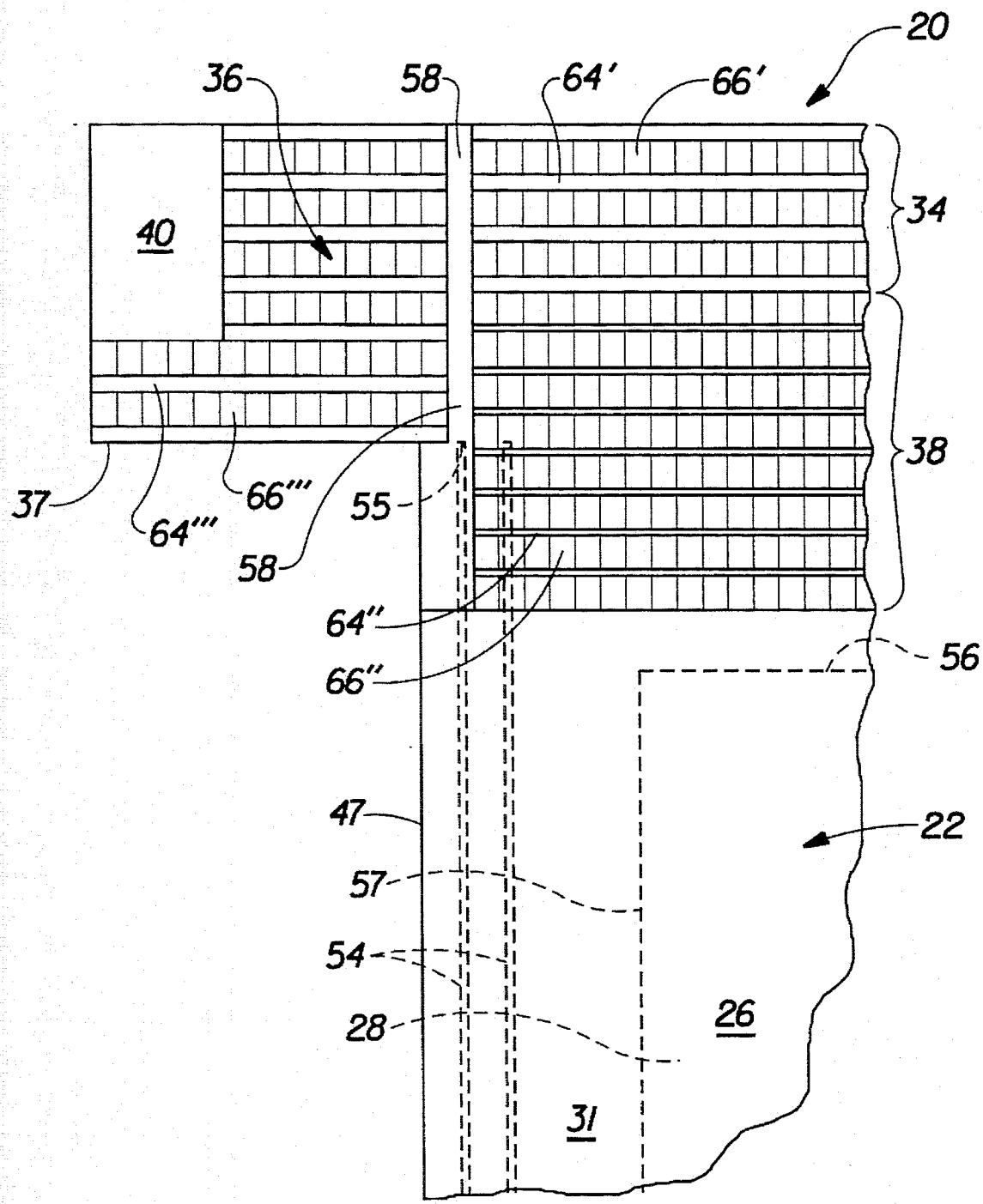
FIG. 4 is a blown up plan view of a portion of the disposable diaper of FIG. 1 showing the details of the SELF webs of the extensible back waist region and the relative positioning of the elements of the diaper.

The central waistband panel 34 is extensible in at least one direction, preferably in a direction having a vector component in the lateral direction, more preferably in the lateral direction, to provide better fit. It should be noted, however, that the central waistband panel may be extensible in any other direction or in more than one direction. In addition, the central waistband panel may have one or more discrete zones of extensibility. For example, as is shown in FIG. 4, the central waistband panel 34 may have a pair of non-extensible zones, each positioned laterally outwardly from a central extensible zone or panel. Alternatively, the entire central waistband panel can be extensible to provide the desired functions as described herein.

The side panels 36 are those portions of the extensible back waist feature 32 that extend laterally outwardly from the central waistband panel 34 and at least a portion of the hip panel 38. The side panels 36 are each an extensible member that primarily function to provide a more comfortable and contouring fit by initially conformably fitting the diaper to the wearer at application and sustaining this fit throughout the time of wear well past when the diaper has been loaded with exudates by enlarging the circumference of the diaper at the sides, attaching the back waist region to the front waist region of the diaper to complete a closure for the diaper, and distributing forces along both the waist and legs to transfer these forces such that there is a snug fit with no skin irritation due to excessive forces on the legs or the waist. The side panels provide stretch as well as, in preferred embodiments, a contractive force after extension and application. Thus, the side panels provide a more comfortable and contouring fit by allowing the sides of the diaper to expand and contract. The side panels also develop and maintain wearing forces (tensions) and enhance the tensions developed and maintained by the closure system to maintain the diaper on the wearer and enhance the fit. The side panels assist in maintaining the primary line of tension formed by the primary fastening system; allowing the diaper to conformably fit over the hips of the wearer where there is dynamic motion, and initially pretensioning the front extensible waist feature, if provided on the diaper, since the diaperer typically stretches the side panels when applying the diaper on the wearer so that when the side panels contract, tension is transmitted from the side panels through the waist closure system into the extensible front waist feature. The side panels further provide more effective application of the diaper since even if the diaperer pulls one side panel farther than the other during application, the diaper will "self-adjust" during wear. (While the extensible back waist feature has side panels; the extensible front waist feature may also have side panels, preferably extensible side panels such as are described herein.)

The side panels 36 may have a number of different sizes and shapes. For example, the side panels may each have an arcuate shape so that forces transmitted through the side panel are along a line or zone disposed at an angle to the body of the wearer to fit the diaper into the lumbar curve of the back and to allow the tensional forces (the primary line of tension) to be directed downward toward the abdominal crease of the wearer so as to provide a continuous primary line of tension. Examples of such side panels are described in U.S. patent application Ser. No. 08/072,300 entitled "Absorbent Articles Providing Sustained Dynamic Fit" filed by LaVon, et al. on Jun. 3, 1993; and U.S. patent application Ser. No. 08/155,048 entitled "Absorbent Article With Multi-Directional Extensible Side Panels" filed by Robles, et al. on Nov. 19, 1993; each of which is incorporated herein by reference. In the preferred embodiment shown in FIG. 1A, the side panels 36 have a rectangular shape. For a typical "large" (8 kg to 14 kg) baby diaper, the side panels may, for example, have a size of about 63 mm in the lateral direction by about 57 mm in the longitudinal direction.

The side panels 36 may be constructed in a number of configurations and from a number of different materials. Examples of diapers with elasticized side panels are disclosed in U.S. Pat. No. 4,857,067 issued to Wood, et al. on Aug. 15, 1987; U.S. Pat. No. 4,381,781 issued to Sciaffara, et al. on May 3, 1983; U.S. Pat. No. 4,938,753 issued to Van Gompel, et al. on Jul. 3, 1990; and the hereinbefore referenced U.S. Pat. No. 5,151,091 issued to Buell, et al. on Sep. 21, 1991; each of which are incorporated herein by reference. Thus, the side panels may comprise conventional elastic materials or mechanically stretched laminates such as a zero strain stretch laminate. In a preferred embodiment of the present invention, the side panels comprise a SELF web as described hereinafter.

The side panels 36 may comprise a separate element affixed to the back waist feature 32 at the central waistband panel 34 and the hip panel 38, or can be constructed as an extension of other elements of the back waist feature or the diaper such as the backsheet 26 or the topsheet 24, preferably both the topsheet and the backsheet. In the embodiment of the present invention shown in FIG. 1, the side panels 36 each comprise a separate SELF web joined to the back waist feature (the central waistband panel 34 and the hip panel 38). The SELF web of the side panels, as described hereinafter, preferably comprises a laminate of two or more layers, preferably two layers; most preferably a laminate of a layer of a polyethylene blend film such as is marketed by Clopay Corporation of Cincinnati, Ohio as Clopay 1401 and a nonwoven web such as the P-8 material previously described for use as the topsheet. The extension force of each side panel is preferably between about 10 g/cm to about 15 g/cm at 50% extension.

The side panels 36 are extensible in at least one direction, preferably in a direction having a vector component in the lateral direction, more preferably in the lateral direction, to provide better fit. It should be noted, however, that the side panels may be extensible in any other direction or in more than one direction. In addition, the side panels may have one or more discrete zones of extensibility. Preferably, each entire side panel is extensible to provide the desired functions as described herein.

While each panel of the back waist feature 32 may be constructed from a number of different extensible or elastic materials as are known in the art, one or more, and preferably each, of the panels of the back waist feature, for performance and cost reasons, is preferably constructed of a structural elastic-like film (SELF) web. (The term "web" herein refers to a sheet-like material comprising a single layer of material or a composite or a laminate of two or more layers.)

Figure 5:
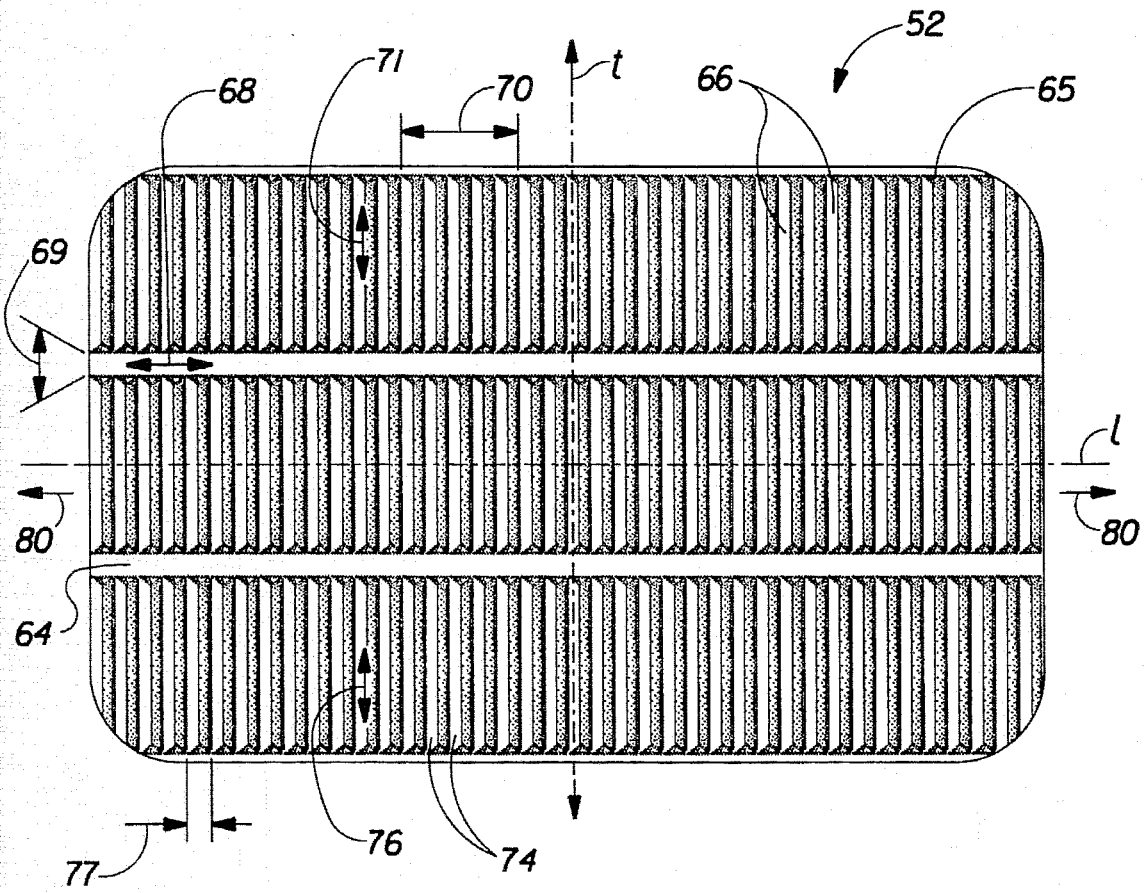
FIG. 5 is a plan view photograph of a preferred embodiment of a SELF web having a strainable network of the present invention with the rib-like elements facing toward the viewer.

FIG. 5 shows an embodiment of a SELF web 52 (formed web material) of the present invention constructed of a single layer of a formed polymeric material. The SELF web 52 is shown in its substantially untensioned condition. The web has two centerlines, a first centerline, l, (which is also referred to as an axis, line, or direction "l") and a second centerline, t, (which is also referred to as an axis, line or direction "t") which is generally perpendicular to the first centerline. The web is comprised substantially of linear low density polyethylene (LLDPE) although it may also be comprised of other polyolefins such as polyethylenes including low density polyethylene (LDPE), ultra low density polyethylene (ULDPE), high density polyethylene (HDPE) or polypropylene and/or blends thereof of the above and other materials. Examples of other suitable polymeric materials include, but are not limited to, polyester, polyurethanes, compostable or biodegradable polymers, and breathable polymers.

Figure 5A:
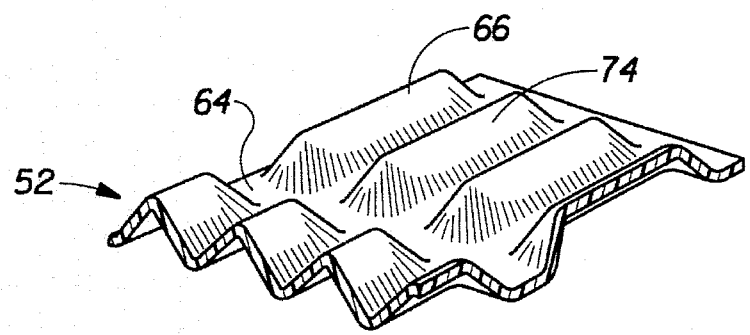
FIG. 5A is a segmented, perspective illustration of the SELF web of FIG. 5 in an untensioned condition.

Referring to FIGS. 5 and 5A, the SELF web includes a "strainable network" of distinct regions. As used herein, the term "strainable network" refers to an interconnected and interrelated group of regions which are able to be extended to some useful degree in a predetermined direction providing the SELF web with an elastic-like behavior in response to an applied and subsequently released elongation. The strainable network includes at least a first region 64 (also generally referred to herein as bands or channels) and a second region 66 (also generally referred to herein as ribs or pleats). The SELF web 52 also includes a transitional region 65 which is at the interface between the first region 64 and the second region 66. The transitional region 65 will exhibit behavior of both the first region and the second region. It is recognized that every embodiment of the present invention will have a transitional region, however preferred embodiments of the present invention will exhibit elastic-like behavior substantially as a result of the first region 64 and the second region 66. Therefore, the ensuing description of the present invention will be concerned with the behavior of the SELF web in the first regions and the second regions only and not the complex behavior of the SELF web in the transitional regions.

SELF web 52 has a first surface and an opposing second surface. In the preferred embodiment shown in FIGS. 5 and 5A, the strainable network includes a plurality of first regions 64 and a plurality of second regions 66. The first regions 64 have a first axis 68 and a second axis 69, wherein the first axis 68 is preferably longer than the second axis 69. The first axis 68 of the first region 64 is substantially parallel to the first axis of the SELF web 52 while the second axis 69 is substantially parallel to the second axis of the SELF web 52. The second regions 66 have a first axis 70 and a second axis 71. The first axis 70 is substantially parallel to the first axis of the SELF web 52, while the second axis 71 is substantially parallel to the second axis of the SELF web 52. In the preferred embodiment of FIG. 5, the first regions 64 and the second regions 66 are substantially linear, extending continuously in a direction substantially parallel to the first axis of the SELF web 52.

The first region 64 has an elastic modulus E1 and a cross-sectional area A1. The second region 66 has an elastic modulus E2 and a cross-sectional area A2.

In the illustrated embodiment, the SELF web 52 has been "formed" such that the SELF web 52 exhibits a resistive force along a axis, which in the case of the illustrated embodiment is substantially parallel to the first axis of the SELF web, when subjected to an applied axial elongation in a direction substantially parallel to the first axis. As used herein, the term "formed" refers to the creation of a desired structure or geometry upon the SELF web that will substantially retain the desired structure or geometry when it is not subjected to any externally applied elongations or forces. A SELF web of the present invention is comprised of at least a first region and a second region, wherein the first region is visually distinct from the second region. As used herein, the term "visually distinct" refers to features of the SELF web which are readily discernible to the normal naked eye when the SELF web or objects embodying the SELF web are subjected to normal use. A SELF web of the present invention is comprised of a strainable network of contiguous, "distinct", and "dissimilar" regions, wherein the strainable network includes at least a first region and a second region, where the first region has a "surface-pathlength" less than that of the second region, as measured parallel to a predetermined axis when the material is in an untensioned state. As used herein, the term "formed portion" refers to the portion of the material which is comprised of the desired structure or geometry of the strainable network. As used herein, the term "surface-pathlength" refers to a measurement along the topographic surface of the region in question in a direction parallel to the predetermined axis. As used herein, the term "distinct" or "dissimilar" when referring to regions, refers to regions within the strainable network having measurably different surface-pathlengths as measured parallel to a predetermined axis while the SELF web is in an untensioned condition. The method for determining the surface-pathlength of the respective regions can be found in the test methods section set forth in subsequent portions of the specification.

Methods for forming materials include, but are not limited to, embossing by mating plates or rolls, thermoforming, high pressure hydraulic forming, or casting. While in embodiments as are shown in FIGS. 5 and 5A the entire SELF web has been formed, the present invention may also be practiced by forming only a portion thereof.

In the preferred embodiment shown in FIGS. 5 and 5A, the first regions 64 are substantially planar. That is, the material within the first region 64 is in substantially the same condition before and after the formation step undergone by the SELF web 52. The second regions 66 include a plurality of rib-like elements 74. The rib-like elements may be embossed, debossed or a combination thereof.

The rib-like elements 74 have a first or major axis 76 which is substantially parallel to the second axis of the SELF web and a second or minor axis 77 which is substantially parallel to the first axis of the SELF web 52. The first axis 76 of the rib-like elements 74 is at least equal to, and preferably longer than the second axis 77. To enhance the two-stage resistive force versus elongation behavior characteristics of the panels of the diaper of the present invention, the ratio of the first axis 76 to the second axis 77 is at least 1:1, preferably at least 2:1, or greater. In general, the greater this ratio, the more pronounced will be the two-stage resistive force versus elongation characteristic of the SELF web.

The first region 64 and the second region 66 each have a "projected pathlength". As used herein, the term "projected pathlength" refers to the length of a shadow of a region that would be thrown by parallel light. The projected pathlength of the first region 64 and the projected pathlength of the second region 66 are equal to one another.

The first region 64 has a surface-pathlength, L1, less than the surface-pathlength, L2, of the second region 66 as measured topographically in a direction parallel to the first axis of the SELF web while the SELF web is in an untensioned condition. To enhance the two-stage resistive force versus elongation behavior characteristic of the SELF web having strainable networks of the present invention, the surface-pathlength of the second region 66 is at least about 15 percent greater than that of the first region, more preferably at least about 30 percent greater than that of the first region, and most preferably at least about 70 percent greater than that of the first region. In general, the greater the surface-pathlength of the second region, the greater will be the elongation of the SELF web.

What makes the SELF web particularly well suited for use as the panels of the diaper, and particularly the extensible back waist feature 32, is that it exhibits a modified "Poisson lateral contraction effect" substantially less than that of an otherwise identical base web of similar material composition. As used herein, the term "Poisson lateral contraction effect" describes the lateral contraction behavior of a material which is being subjected to an applied elongation. The method for determining the Poisson lateral contraction effect of a material can be found in the test methods section set forth in subsequent portions of the specification. Preferably, the Poisson lateral contraction effect of the SELF web of the present invention is less than about 0.4 when the web is subjected to about 20 percent elongation. Preferably, the SELF web exhibits a Poisson lateral contraction effect less than about 0.4 when the SELF web is subjected to about 40, 50 or even 60 percent elongation. More preferably, the Poisson lateral contraction effect is less than about 0.3 when the SELF web is subjected to 20, 40, 50 or 60 percent elongation. The Poisson lateral contraction effect of SELF webs of the present invention is determined by the amount of the web material which is occupied by the first and second regions, respectively. As the area of the SELF web occupied by the first region increases, the Poisson lateral contraction effect also increases. Conversely, as the area of the SELF web occupied by the second region increases the Poisson lateral contraction effect decreases. Preferably, the percent area of the SELF web occupied by the first areas is from about 2% to about 90%, and more preferably from about 5% to about 50%.

Web materials of the prior art which have at least one layer of elastomeric film material will generally have a large Poisson lateral contraction effect, i.e., they will "neck down" as they elongate in response to an applied force. SELF web materials of the present invention can be designed to moderate if not substantially eliminate the Poisson lateral contraction effect of film-based elastomeric webs of the prior art.

For the SELF web 52, the direction of applied axial elongation, D, indicated by arrows 80, in FIG. 5, is substantially perpendicular to the first axis 76 of the rib-like elements 74. As the rib-like elements 74 are able to unbend or geometrically deform in a direction substantially perpendicular to their first axis 76, the direction of applied axial elongation to cause extension in the SELF web 52 is also substantially perpendicular to the first axis 76 of the rib-like elements 74.

While the direction of applied axial elongation D indicated by arrows 80 is substantially perpendicular to the first axis 76 of the rib-like elements 74, an applied axial elongation having a first axis component will cause the SELF web 52 to extend in the direction of applied axial elongation.

Figure 6:
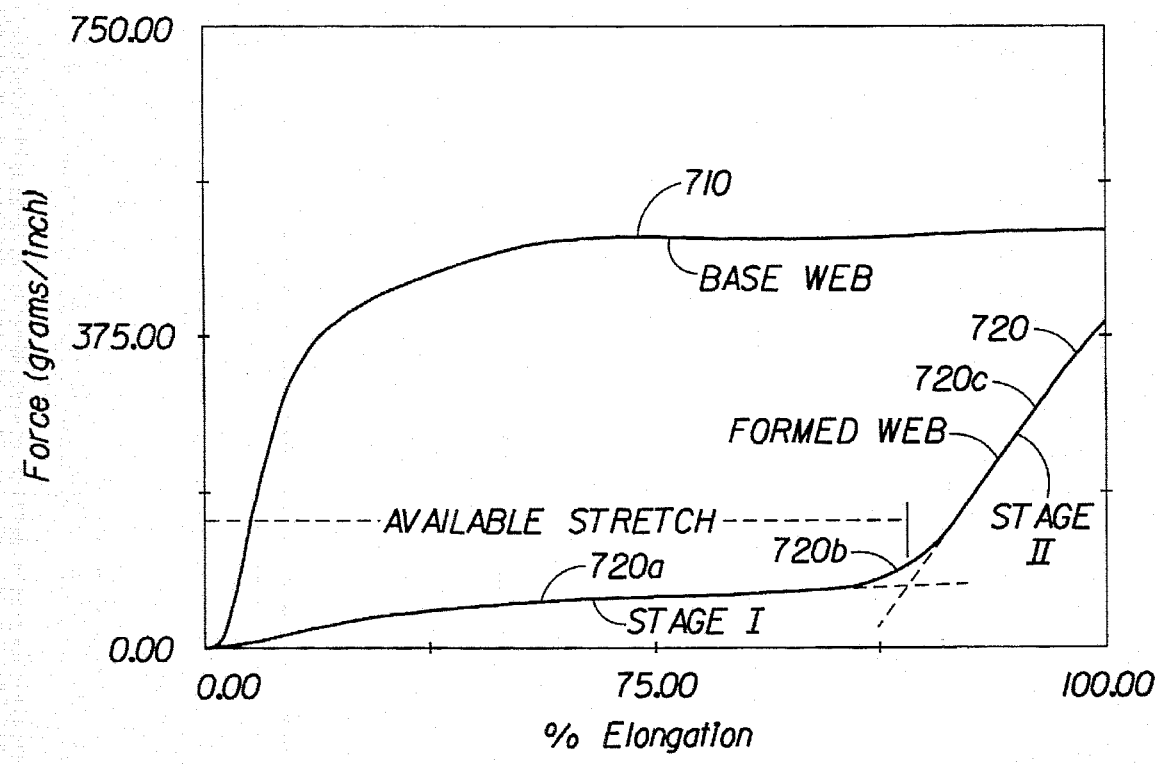
FIG. 6 is a graph of the resistive force versus percent elongation comparing the behavior of the SELF web of the present invention as shown in FIG. 5, with an otherwise identical, planar, base polymeric web material.

In FIG. 6 there is shown a graph of the resistive force-elongation curve 720 of a formed polymeric SELF web of the present invention shown in FIG. 5 along with a curve 710 for a base film of similar composition. Specifically, the samples are polymeric web materials comprised substantially of linear low density polyethylene, approximately 0.001 inches thick, designated Sample 1401 available from Clopay of Cincinnati, Ohio. The method for generating the resistive force-elongation curves can be found in the test methods section set forth in subsequent portions of the specification. Referring now to the force-elongation curve 720, there is an initial substantially linear, lower force versus elongation stage I designated 720a, a transition zone designated 720b, and a substantially linear stage II designated 720c which displays substantially higher force versus elongation behavior.

As seen in FIG. 6, a SELF web exhibits different elongation behavior in the two stages when subjected to an applied elongation in a direction parallel to the first axis of the SELF web. The resistive force to the applied elongation is significantly different between stage I (720a) and stage II (720c) of curve 720 as compared to curve 710 which does not exhibit this behavior. As seen in FIG. 6, the SELF web exhibits different elongation behavior in the two stages when subjected to an applied elongation in a direction parallel to the first axis of the SELF web. The resistive force exerted by the SELF web to the applied elongation is significantly less in the stage I region (720a) versus the stage II region (720c) of curve 720. Furthermore, the resistive force exerted by the SELF web to the applied elongation as depicted in stage I (720a) of curve 720 is significantly less than the resistive force exerted by the base web as depicted in curve 710 within the limits of elongation of stage I. As the SELF web is subjected to further applied elongation and enters stage II (720c) the resistive force exerted by the SELF web increases and approaches the resistive force exerted by the base web. The resistive force to the applied elongation for the stage I region (720a) of the SELF web is provided by the molecular-level deformation of the first region of the SELF web and the geometric deformation of the second region of the SELF web. This is in contrast to the resistive force to an applied elongation that is provided by the base web depicted in curve 710 of FIG. 6, which results from molecular-level deformation of the entire web. SELF web materials of the present invention can be designed to yield virtually any resistive force in stage I which is less than that of the base web material by adjusting the percentage of the web surface which is comprised of the first and second regions, respectively. The force-elongation behavior of stage I can be controlled by adjusting the width, thickness, and spacing of the first region and the composition of the base web.

Figure 5B:
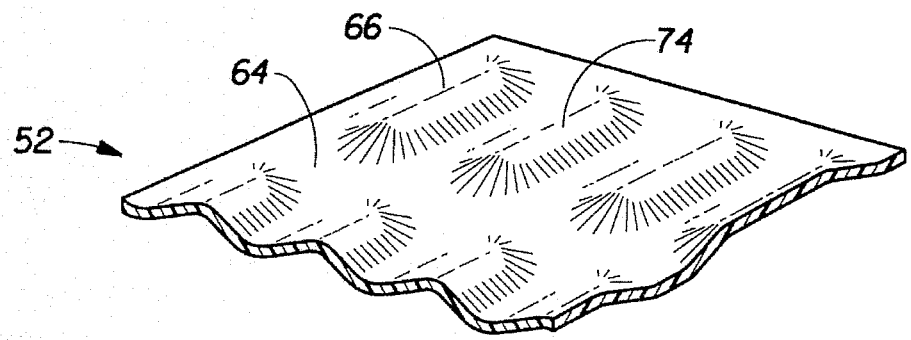
FIG. 5B is a segmented, perspective illustration of the SELF web of FIG. 5 in a tensioned condition corresponding to stage I on the force-elongation curve depicted in FIG. 6.
Figure 5C:
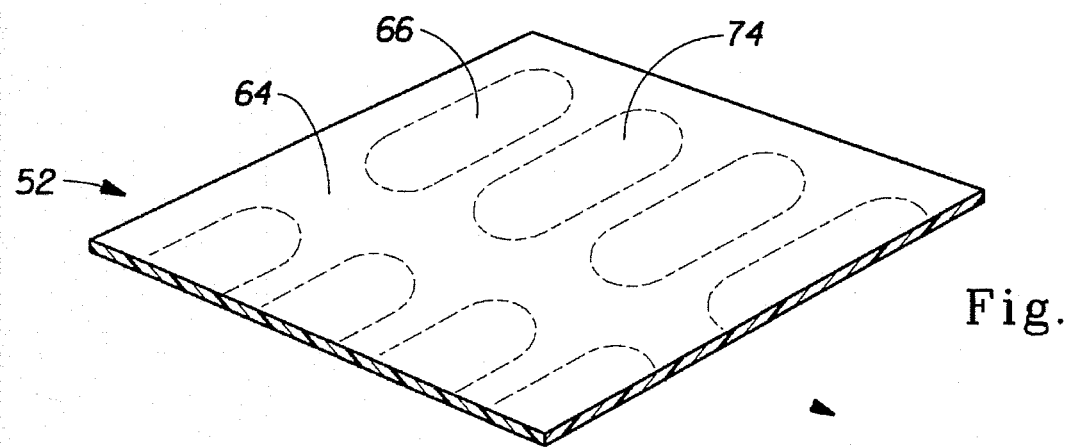
FIG. 5C is a segmented perspective illustration of the SELF web of FIG. 5 in a tensioned condition corresponding to stage II on the force-elongation curve depicted in FIG. 6.

Referring now to FIG. 5B, as the SELF web is subjected to an applied axial elongation, D, indicated by arrows 80 in FIG. 5, the first region 64 having the shorter surface-pathlength, L1, provides most of the initial resistive force, P1, as a result of molecular-level deformation, to the applied elongation which corresponds to stage I. While in stage I, the rib-like elements 74 in the second region 66 are experiencing geometric deformation, or unbending and offer minimal resistance to the applied elongation. In the transition zone (720b) between stages I and II, the rib-like elements 74 are becoming aligned with the applied elongation. That is, the second region is exhibiting a change from geometric deformation to molecular-level deformation. This is the onset of a force wall. In stage II, as seen in FIG. 5C, the rib-like elements 74 in the second region 66 have become substantially aligned with the plane of applied elongation (the second region has reached its limit of geometric deformation) and begin to resist further elongation via molecular-level deformation. The second region 66 now contributes as a result of molecular-level deformation in stage II a second resistive force, P2, to further elongation. The resistive forces to elongation provide a total resistive force, PT, which is greater than the resistive force depicted in stage I. Accordingly, the general slope of the force-elongation curve in stage II is significantly greater than the general slope of the force-elongation curve in stage I.

The resistive force P1 is substantially greater than the resistive force P2 when (L1+D) is less than L2. While (L1+D) is less than L2 the first region 64 provides an initial resistive force, P1, generally satisfying the equation:

$$P1 = \frac{(A1*E1*D)}{L1}$$

When (L1+D) is greater than L2 the first and second regions provide a combined total resistive force, PT, to the applied elongation, D, generally satisfying the equation:

$$PT = \frac{(A1*E1*D)}{L1} + \frac{(A2*E2*|L1 + D - L2|)}{L2}$$

The maximum elongation occurring while in stage I is considered to be the "available stretch" of the SELF web. The available stretch corresponds to the distance over which the second region experiences geometric deformation. The available stretch can be effectively determined by inspection of the force-elongation curve 720 as shown in FIG. 6. The approximate point at which there is an inflection in the transition zone between stage I and stage II is the percent elongation point of "available stretch". The range of available stretch can be varied from about 10% to 100% or more; this range of elongation is often found to be of interest in disposable absorbent articles, and can be largely controlled by the extent to which surface-pathlength L2 in the second region 66 exceeds surface-pathlength L1 in the first region 64 and the properties (composition) of the base film. The term available stretch is not intended to apply a limit to the elongation which the web of the present invention may be subjected to as there are applications where elongation beyond the available stretch is desirable. Significantly higher forces are required to achieve percent elongations in the base film equivalent to those percent elongations in the SELF web 52. The approximate extent of stage I can be controlled as desired by adjusting the pathlengths, L1 and L2, in an untensioned condition. The force-elongation behavior of stage I can be controlled by adjusting the width, thickness, and spacing of first region 64 and the properties of the base film.

Figure 7:
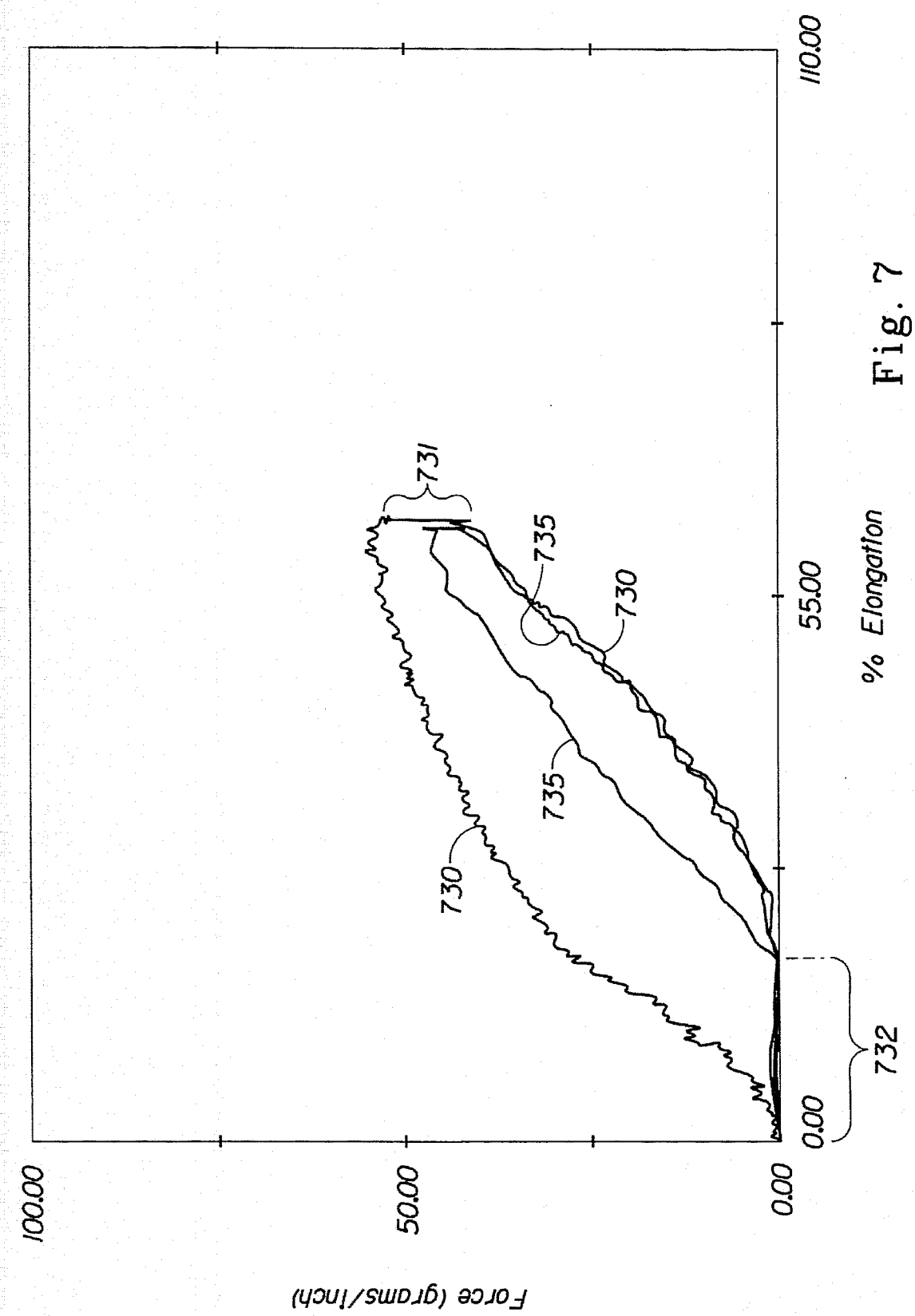
FIG. 7 is a graph of the elastic hysteresis behavior of the SELF web of FIG. 6 when subjected to 60% elongation and examined for hysteresis response.

The curve 730 and 735 in FIG. 7 depicts the elastic hysteresis behavior exhibited by the SELF web of FIG. 5. The sample is the same as in FIG. 6 (Clopay 1401). The sample was examined for elastic hysteresis behavior at an elongation of 60%. Curve 730 represents the response to an applied and released elongation during the first cycle and curve 735 represents the response to applied and released elongation during the second cycle. The force relaxation during the first cycle 731 and the percent set 732 are depicted in FIG. 7. Note that significant recoverable elongation, or useful elasticity, is exhibited at relatively low forces over multiple cycles, i.e., this means the SELF web can easily expand and contract to a considerable degree. The method for generating the elastic hysteresis behavior can be found in the test method section in the subsequent portion of the specification.

When the SELF web is subjected to an applied elongation, the SELF web exhibits an elastic-like behavior as it extends in the direction of applied elongation and retracts to its substantially untensioned condition once the applied force is removed, unless extended beyond the point of yielding. The SELF web is able to undergo multiple cycles of applied elongation without losing its ability to substantially recover. Accordingly, the SELF web is able to return to its substantially untensioned condition once the applied elongation or force is removed.

While the SELF web may be easily and reversibly extended in the direction of applied axial elongation, in a direction substantially perpendicular to the first axis 76 of the rib-like elements 74, the SELF web is not as easily extended in a direction substantially parallel to the first axis of the rib-like elements. The formation of the rib-like elements allows the rib-like elements to geometrically deform in a direction substantially perpendicular to the first or major axis of the rib-like elements, while requiring substantially molecular-level deformation to extend in a direction substantially parallel to the first axis of the rib-like elements.

The amount of applied force required to extend the SELF web is dependent upon the composition and thickness of the base material forming the SELF web and the width and spacing of the first regions, with narrower and more widely spaced first regions requiring lower applied extension forces to achieve the desired elongation for a given composition and thickness. The first axis 68, (i.e., the length) of the undeformed regions 64 is preferably greater than the second axis 69, (i.e., the width) with a preferred length to width ratio of about 5:1 or greater.

The depth and number of rib-like elements 74 can also be varied to control the extension force and available stretch of the SELF web of the present invention. The available stretch or elongation is increased if for a given number of rib-like elements, the height or degree of formation imparted on the rib-like elements is increased. Similarly, the available stretch or elongation is increased if for a given height or degree of formation, the number or frequency of rib-like elements is increased.

There are several functional properties that can also be controlled through the application of the present invention. There is the resistive force exerted by the SELF web against an applied elongation, and the available stretch of the SELF web material before the force wall is encountered. The resistive force that is exerted by the SELF web against an applied elongation is a function of the material composition and thickness and the percent of the projected surface area of the SELF web that is occupied by the first region. The higher the percent area coverage of the SELF web by the first region, the higher resistive force that the SELF web will exert against an applied elongation for a given material composition and thickness. The percent coverage of the SELF web by the first region is determined in part if not wholly by the width of the first region and the spacing between adjacent first regions.

The available stretch of the SELF web is determined by the surface-pathlength of the second region. This is determined at least in part by the rib-like elements spacing, rib-like element frequency, and depth of formation of the rib-like elements as measured perpendicular to the plane of the SELF web. In general, the greater the surface-pathlength of the second region, the greater the available stretch of the SELF web.

While an entire SELF web of the present invention may include a strainable network of first and second regions, the present invention may also be practiced by providing only specific portions of the SELF web with a strainable network comprised of first and second regions. For example, as shown in FIGS. 1 and 4, only portions of the central waistband panel and hip panel of the extensible back waist region comprise the SELF web. Portions of the central waistband panel and the hip panel also comprise the base laminate as described herein.

The configuration and spacing of the first and second regions may also be varied to vary the characteristics of the resultant SELF web. For example, the second regions may comprise curvilinear rib-like elements, the first regions and the second regions may be curvilinear, or the first regions may be curvilinear. The SELF web may also exhibit an elastic-like behavior along a plurality of axes by extending the axes in a radial, fan-like array to allow the SELF web to exhibit an elastic-like behavior along a plurality of axes. For example, the multiple axes may be positioned at various angles to one another such as 45°, 90°, 135°, etc. In addition to the various angles of orientation, the regions themselves may be straight, curvilinear or combinations thereof. The surface pathlengths in the second region may also provide a difference in amplitude of the rib-like elements such that the SELF web will have different zones of available stretch. It is also possible that the rib-like elements can be varied between adjacent regions to provide different available stretches in the adjacent second regions. The widths of the first region may also vary across the web with the narrower regions offering a lower resistive force to an applied elongation as compared to the higher resistive force offered by the wider first region.

The SELF web also need not be extensible only in the direction parallel to the lateral centerline of the diaper as is shown in FIG. 1. For example, the first axis and the second axis of the SELF web may be disposed at an angle to the longitudinal centerline and lateral centerline of the diaper 20, respectively. Thus, the SELF web would axially elongate along a line at an angle to the lateral centerline of the diaper. This angle is preferably between about 0° and about 30° for the diapers of the present invention. Further, portions of the SELF web may have different angles of extensibility. For example, in the side panels, a portion of the side panel closest to the end edge of the diaper, the waist panel, may be extensible in a direction parallel to the lateral centerline of the diaper; however, the portion of the SELF web closest to the lateral centerline, the thigh panel, may have an extensibility nonparallel to the direction of extensibility of the waist panel such that it is disposed at an angle to the lateral centerline. This multi-directional SELF panel can provide improved waist and leg conformity.

Figure 8:
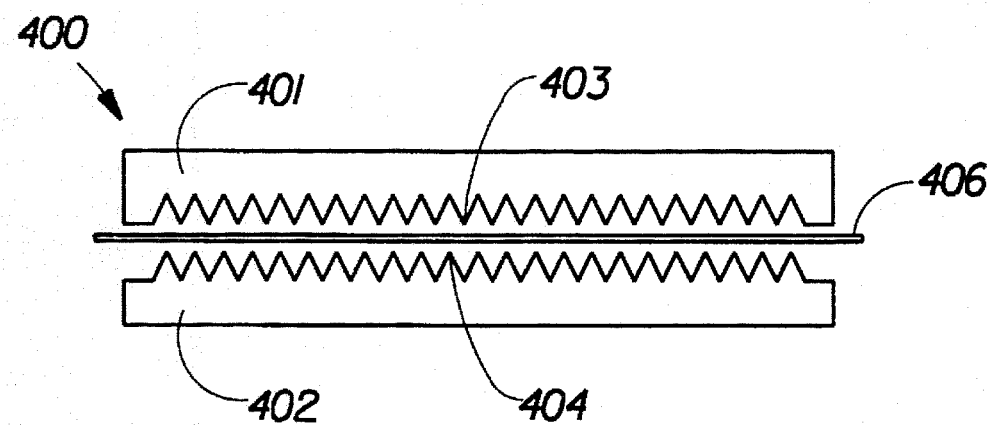
FIG. 8 is a simplified side elevational view of a preferred apparatus used to form that portion of the SELF web of the present invention.

Referring now to FIG. 8, there is shown an apparatus 400 used to form the SELF web 52 shown in FIG. 5. Apparatus 400 includes plates 401, 402. Plates 401, 402 include a plurality of intermeshing teeth 403, 404, respectively. Plates 401, 402 are brought together under pressure to form the base film 406.

Figure 9:
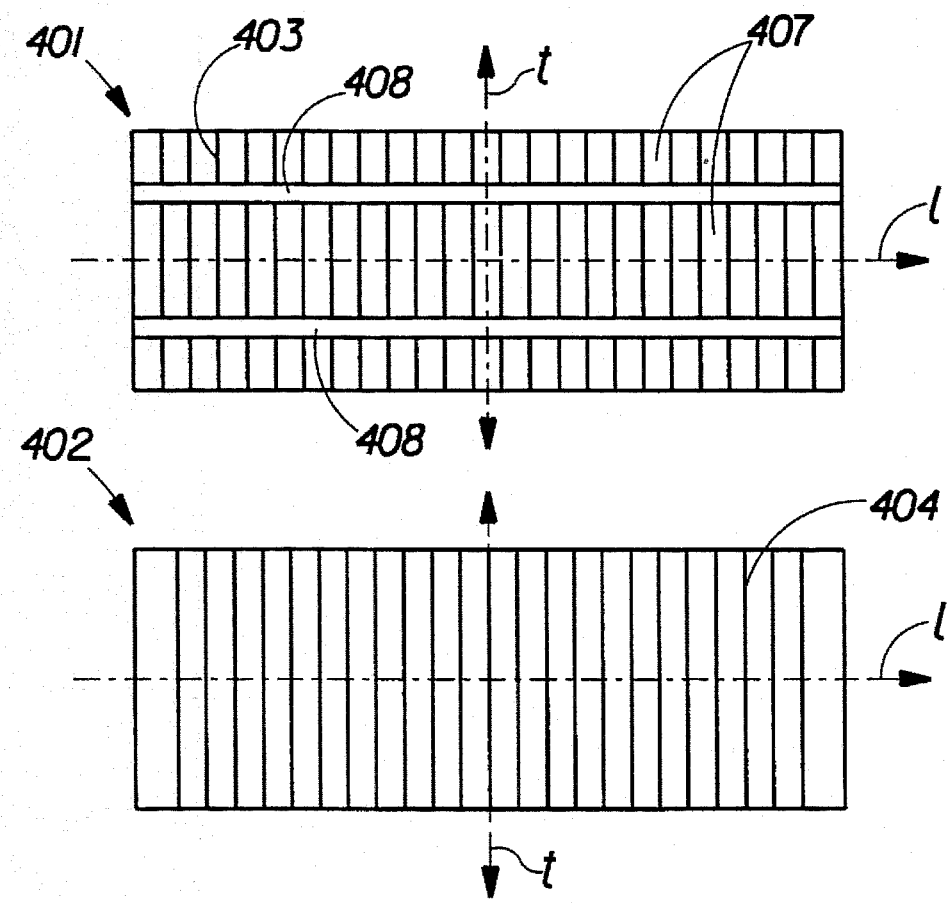
FIG. 9 is a plan view of the opposed meshing plates of the apparatus of FIG. 8 laid side-by-side with their meshing surfaces exposed.

Referring now to FIG. 9, it can be seen that plates 401 and 402 each have a first axis "l" and a second axis "t" which is substantially perpendicular to the first axis. Plate 401 includes toothed regions 407 and grooved regions 408 both which extend substantially parallel to the first axis of the plate 401. Within toothed regions 407 of plate 401 there are a plurality of teeth 403. Plate 402 includes teeth 404 which mesh with teeth 403 of plate 401. When the base film 406 is formed between plates 401, 402 the portions of the base film 406 which are positioned within grooved regions 408 of plate 401 and teeth 404 on plate 402 remain undeformed. These regions correspond with the first regions 64 of the SELF web 52 shown in FIG. 5. The portions of the base film 406 positioned between toothed regions 407 of plate 401 and teeth 404 of plate 402 are incrementally and plastically formed creating rib-like elements 74 in the second regions 66 of the SELF web 52.

Figure 10:
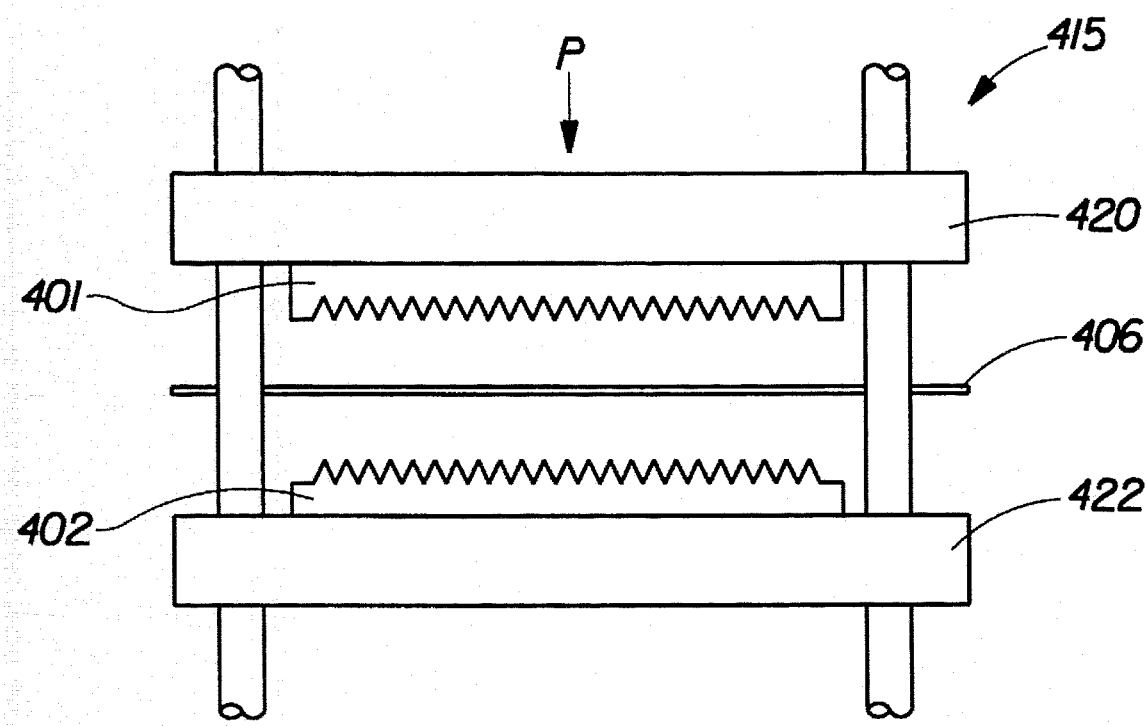
FIG. 10 is a simplified side elevational view of a static press used to form at least a portion of the base film into a SELF web of the present invention.

The method of formation can be accomplished in a static mode, where one discrete portion of a base film is deformed at a time. An example of such a method is shown in FIG. 10. A static press indicated generally as 415 includes an axially moveable plate or member 420 and a stationary plate 422. Plates 401 and 402 are attached to members 420 and 422, respectively. While plates 401 and 402 are separated, base film 406 is introduced between the plates, 401, 402. The plates are then brought together under a pressure indicated generally as "P". The upper plate 401 is then lifted axially away from plate 402 allowing the formed SELF web 408 to be removed from between plates 401 and 402.

Figure 11:
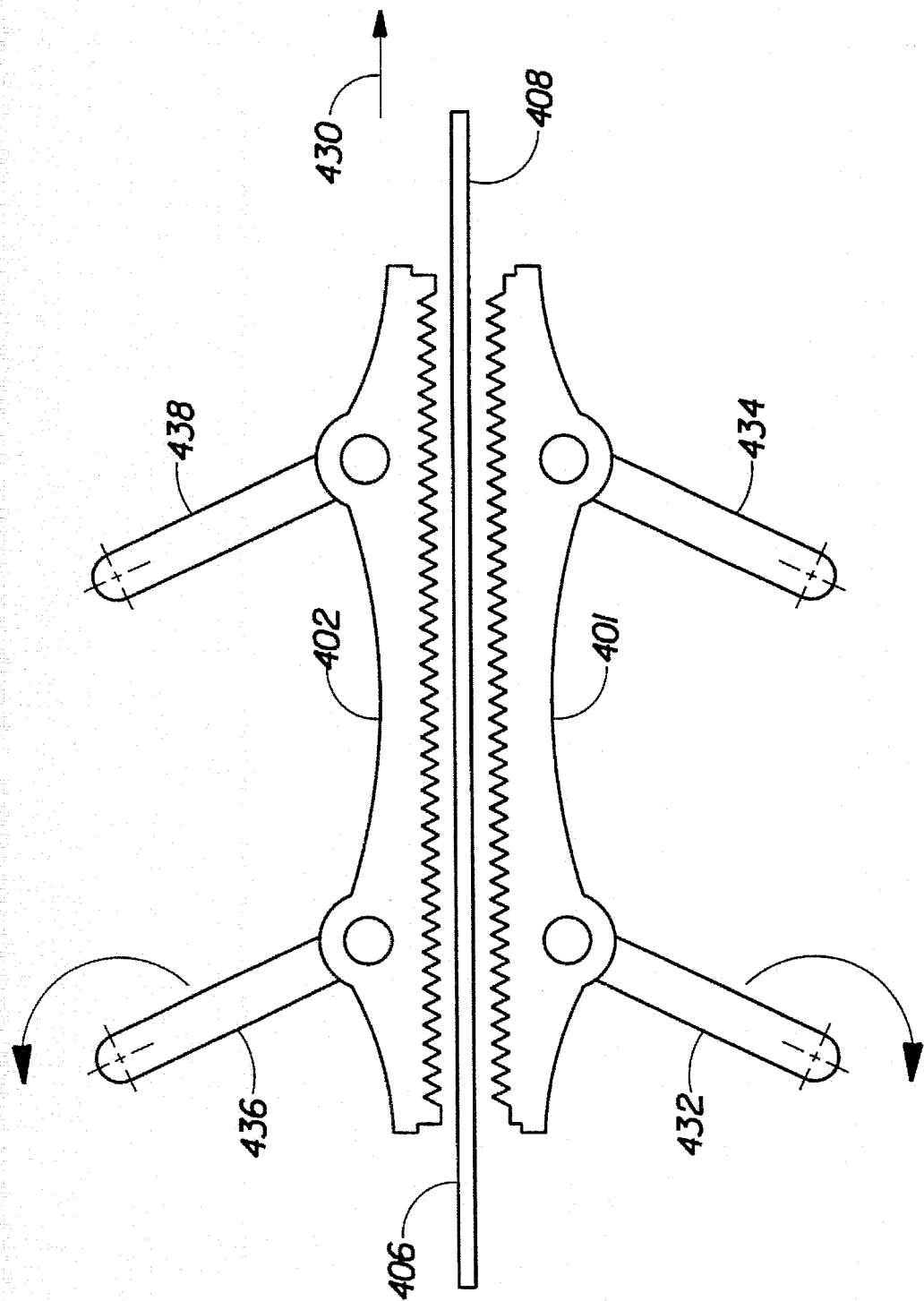
FIG. 11 is a simplified side elevational view of a continuous, dynamic press used to form predetermined portions of the base film into a SELF web of the present invention.

FIG. 11 is an example of a continuous, dynamic press for intermittently contacting the moving web and forming the base material 406 into a formed web similar to the SELF web 52 of FIG. 5. Polymeric film 406 is fed between plates 401 and 402 in a direction generally indicated by arrow 430. Plate 401 is secured to a pair of rotatably mounted arms 432, 434 which travel in a clockwise direction which move plate 401 in a clockwise motion. Plate 402 is connected to a pair of rotary arms 436, 438 which travel in a counter clockwise direction moving plate 402 in a counter clockwise direction. Thus, as web 406 moves between plates 401 and 402 in direction indicated by arrow 430, a portion of the base film between the plates is formed and then released such that the plates 401 and 402 may come back grab and form another section of base film 406. This method has the benefit of allowing virtually any pattern of any complexity to be formed in a continuous process, e.g., uni-directional, bi-directional, and multi-directional patterns.

The dynamic press of FIG. 11 could be used on a completed absorbent article to form strainable networks into the completed product. For example, the entire or portions of the completed absorbent article could be placed between plates 401 and 402 to create a strainable network in all layers of the absorbent article.

Another method of forming the base material into a SELF web is vacuum forming. An example of a vacuum forming method is disclosed in commonly assigned U.S. Pat. No. 4,342,314, issued to Radel et al. on Aug. 3, 1982. Alternatively, the SELF web of the present invention may be hydraulically formed in accordance with the teachings of commonly assigned U.S. Pat. No. 4,609,518 issued to Curro et al. on Sep. 2, 1986. Each of the above patents are being incorporated herein by reference.

Figure 12:
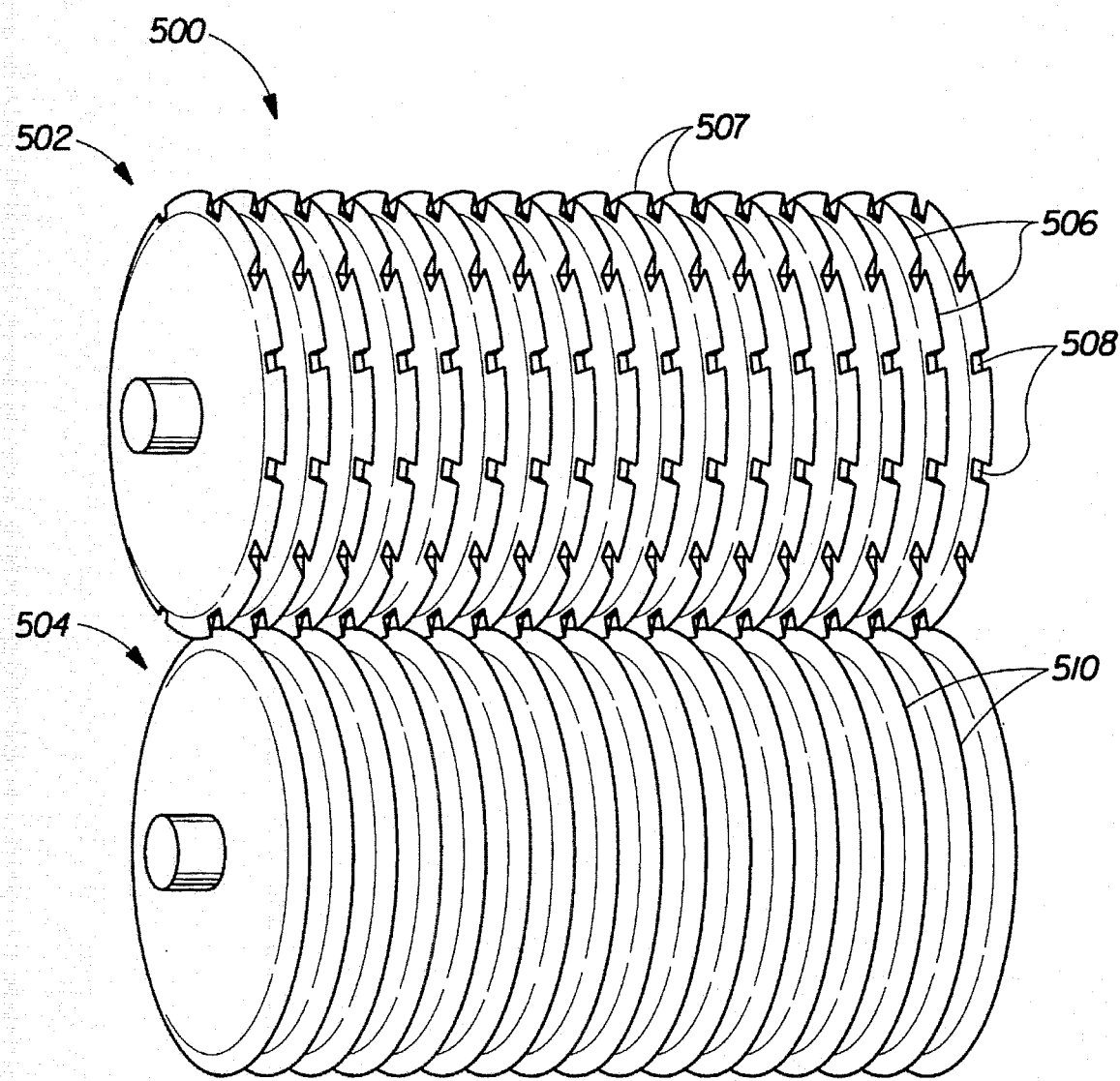
FIG. 12 is a simplified illustration of an apparatus used to form at least a portion of a base film into a SELF web of the present invention.

In FIG. 12 there is shown another apparatus generally indicated as 500 for forming the base film into a formed SELF web. Apparatus 500 includes a pair of rolls 502, 504. Roll 502 includes a plurality of toothed regions 506 and a plurality of grooved regions 508 that extend substantially parallel to an axis running through the center of the cylindrical roll 502. Toothed regions 506 include a plurality of teeth 507. Roll 504 includes a plurality of teeth 510 which mesh with teeth 507 on roll 502. As a base polymeric film is passed between intermeshing rolls 502 and 504, the grooved regions 508 will leave portions of the film unformed producing the first regions 64 of the SELF web 52. The portions of the film passing between toothed regions 506 and teeth 510 will be formed by teeth 507 and 510, respectively, producing rib-like elements 74 in the second regions 66 of the SELF web 52.

Alternatively, roll 504 may consist of a soft rubber. As the base film is passed between toothed roll 502 and rubber roll 504 the film is mechanically formed into the pattern provided by the toothed roll 502. The film within the grooved regions 508 will remain unformed, while the film within the toothed regions 506 will be formed producing rib-like elements of the second region.

Figure 13:
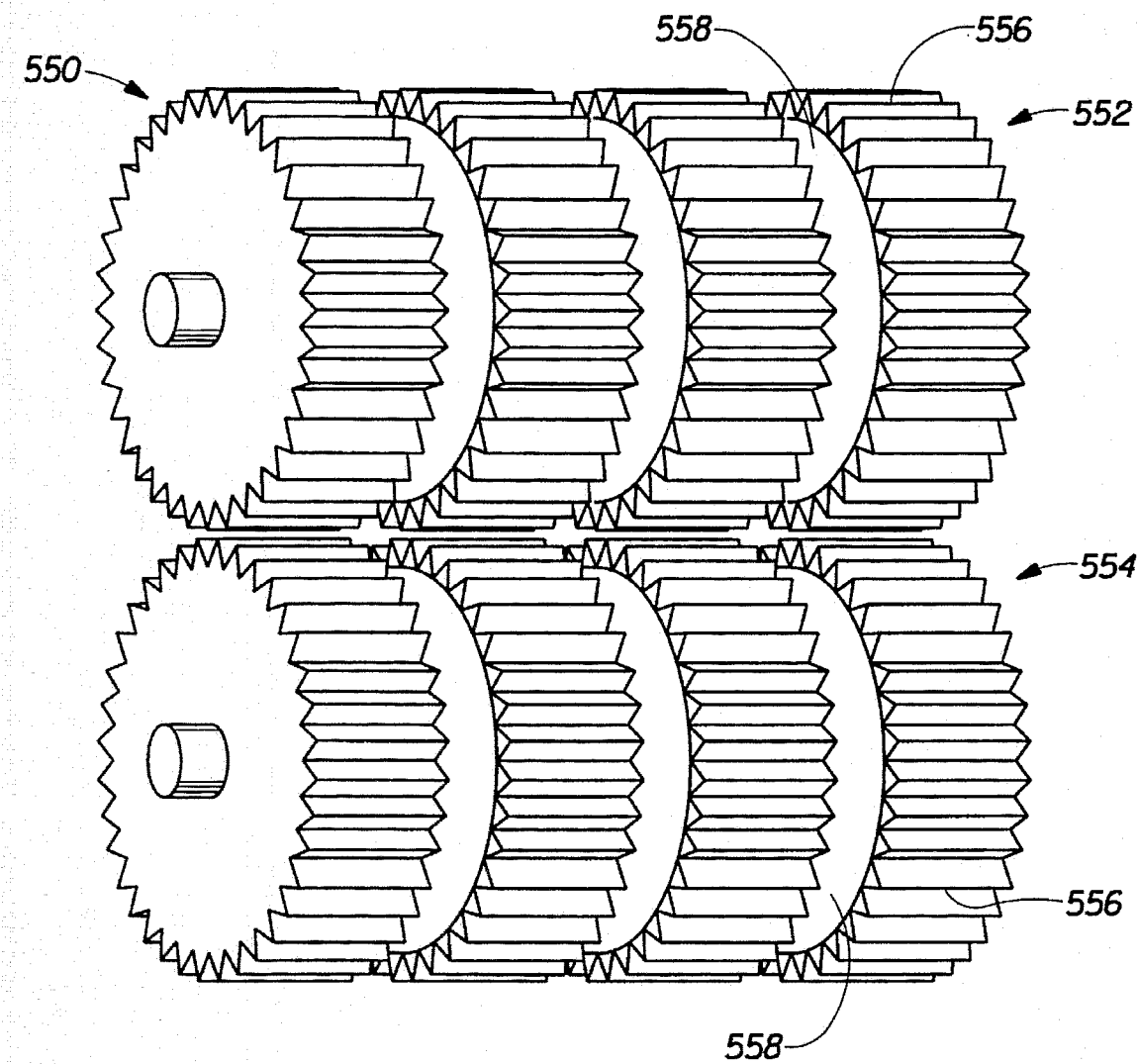
FIG. 13 is a simplified illustration of yet another apparatus used to form at least a portion of a base film into a SELF web of the present invention.

Referring now to FIG. 13, there is shown an alternative apparatus generally indicated as 550 for forming the base film into a SELF web in accordance with the teachings of the present invention. Apparatus 550 includes a pair of rolls 552, 554. Rolls 552 and 554 each have a plurality of toothed regions 556 and grooved regions 558 extending about the circumference of rolls 552, 554 respectively. As the base film passes between rolls 552 and 554, the grooved regions 558 will leave portions of the film unformed, while the portions of the film passing between toothed regions 556 will be formed producing rib-like elements 74 in second regions 66.

While the SELF web has been described as a single base layer of substantially planar polymeric film, the present invention may be practiced equally well with other base materials or with laminates of materials. Examples of base materials from which the SELF web of the present invention can be made include two-dimensional apertured films and macroscopically expanded, three-dimensional, apertured formed films. Examples of macroscopically expanded, three-dimensional, apertured formed films are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel, et al. on Aug. 3, 1982; U.S. Pat. No. 4,463,045 issued to Ahr, et al. on Jul. 31, 1984; and U.S. Pat. No. 5,006,394 issued to Baird on Apr. 9, 1991. Each of these patents are incorporated herein by reference. Examples of other suitable base materials include composite structures or laminates of polymer films, nonwovens, and polymer films and nonwovens. The laminates of polymer films and nonwovens may also comprise absorbent or fibrous absorbent materials, foams, or other compositions. Additional reinforcing elements can also be added for strength and recovery benefits.

Base materials comprising laminates of apertured films and nonwoven materials may also be used whereby in the process of forming such materials, the connections between a plurality of the nonwoven fibers are broken up to protrude slightly through the apertures of the apertured film.

It may be desirable in certain embodiments to have the SELF web exhibit a certain degree of bulkiness. Laminates of polymer films with high-loft nonwoven materials, and laminates with multi-layers of nonwovens are ways of providing increased bulk. Other methods for creating bulk include the formation of a single layer of polymer film in the manner of this invention followed by prestretching of the film and subsequent application of the nonwoven to one or both sides while the polymer film is in its prestretched condition. Upon relaxation of the stretch, the nonwoven material forms puckers which give the material added bulk. Another method for making bulky laminates is by forming individual polymeric film layers in the manner of this invention, followed by lamination of multiple layers of these materials. Three dimensionally apertured films that have been formed using the method described herein also provide good bulk in a laminate structure.

Other materials which may be subject to the deformation processes disclosed herein for producing webs which exhibit an elastic-like behavior in the direction of applied force include polymeric foams and thermally bonded air-laid fibrous structures.

Figure 14:
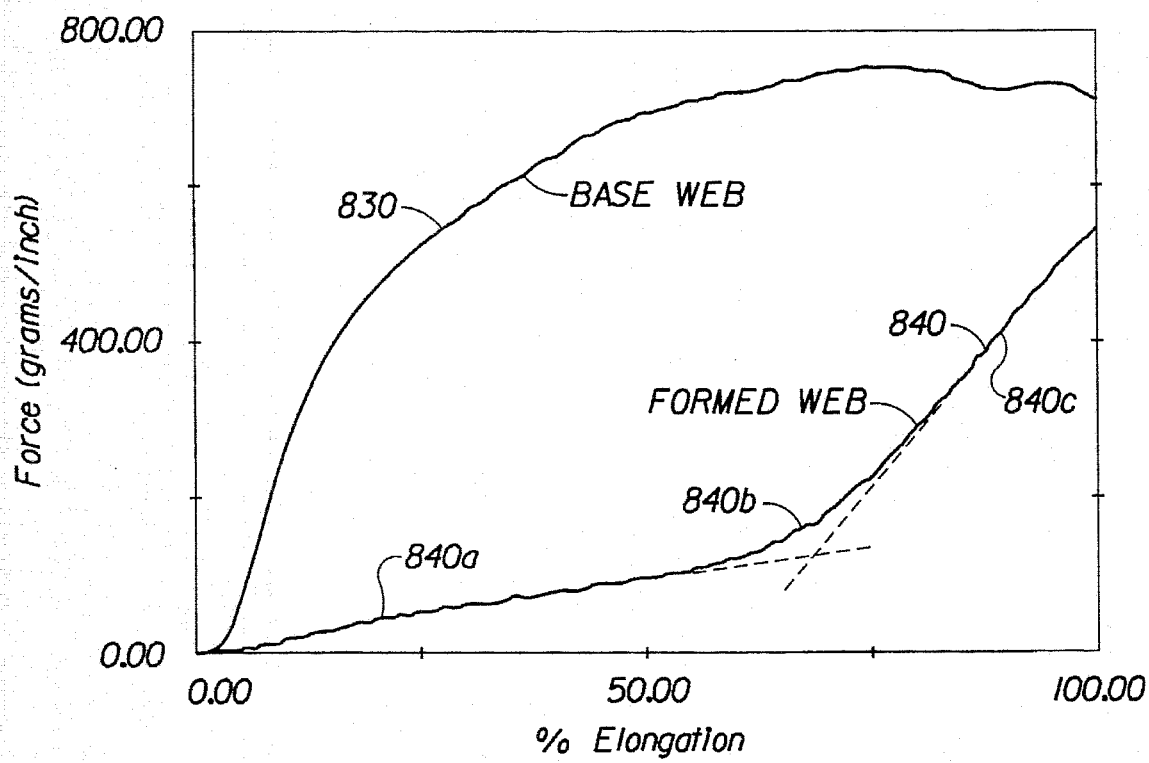
FIG. 14 is a graph of the resistive force vs. percent elongation comparing the behavior of an alternative SELF web material which is a laminate comprised of a layer of a polymeric film and a nonwoven layer secured by adhesive having a strainable network of the present invention to the otherwise identical unformed, planar, base web material.
Figure 15:
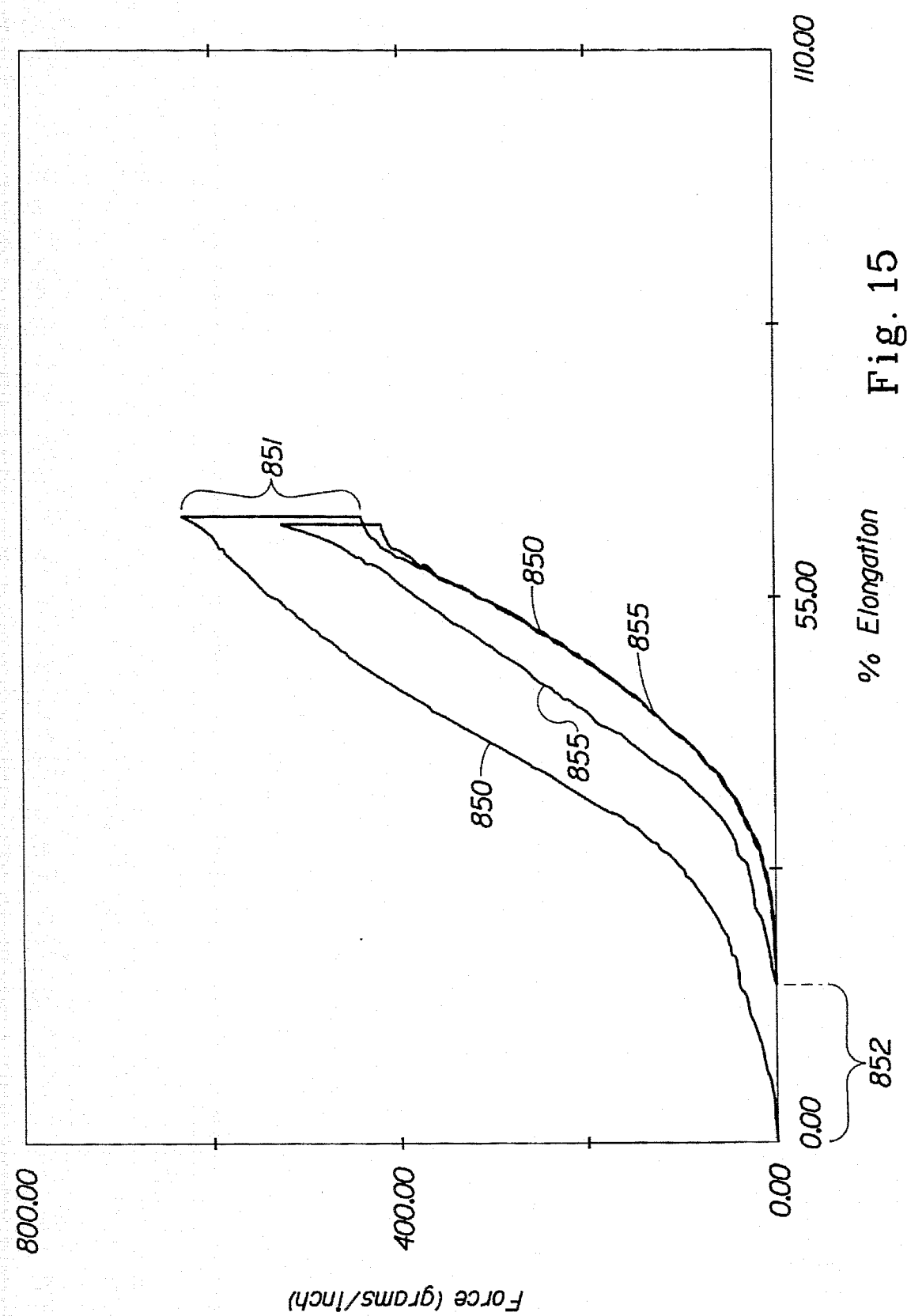
FIG. 15 is a graph of the elastic hysteresis behavior of the web material having the strainable network of FIG. 14 when subjected to 60% percent elongation and examined for elastic hysteresis response.

FIG. 14 shows the force elongation behavior for a base web 830 and the formed SELF web 840 of the present invention wherein both webs are comprised of a laminate of a layer of the Clopay 1401 polyethylene blend film of FIG. 6 adhered via hot melt glue available from Findley Adhesives, of Wauwautosa, Wis., Sample 2301, to a layer of nonwoven material made substantially of polypropylene fibers as is available from Veratec of Walpole, Mass., under the designation P-11. Referring now to curve 840, there is an initial substantially linear, lower force-elongation stage I designated 840A, a transition zone designated 840B, and substantially linear stage II designated 840C. For this laminate web, note the distinctive lower force 2-stage behavior of the formed SELF web as compared to the base web. The curves 850 and 855 in FIG. 15 show the hysteresis behavior of the same type when examined at 60% elongation. Curve 850 represents the response to applied elongation during the first cycle and curve 855 represents the response to applied elongation during the second cycle. The force elongation during the first cycle 851 and the percent set 852 are depicted in FIG. 15. Note that this laminate web exhibits a very significant elastic recovery over the observed range of elongation.

In a preferred embodiment of the present invention, the SELF web comprises a laminate of two layers comprising an inner layer 53 and an outer layer 55. The inner layer 53 is preferably a nonwoven material such as the P-8 material previously described. The outer layer 55 is preferably the base polymeric film as described herein with reference to FIG. 5 (Clopay 1401) or the backsheet (Tredegar P8863). Alternatively, a support layer may be added to provide a three layer laminate. Further, a nonwoven layer may be added over the outer layer to provide a softer feel for the outside of the waist feature. The laminates may be combined by any of a number of bonding methods known to those skilled in the art. Such bonding methods include but are not limited to thermal bonding; adhesive bonding (using any of a number of adhesives including but not limited to spray adhesives, hot melt adhesives, latex based adhesives and the like); sonic bonding; and extrusion laminating whereby a polymeric film is cast directly onto a nonwoven substrate, and while still in a partially molten state, bonds to one side of the nonwoven or where a meltblown nonwoven is directly attached to a polymeric web.

FIG. 4 shows a blown up plan view of the diaper of the present invention showing the specific design of the SELF webs forming the diaper and the relative positioning of each of the panels and other elements forming the diaper. As discussed hereinabove, the width (longitudinal dimension in FIG. 1) of the bands (the channels or first regions) of the SELF web is used to control the extension forces and the available stretch of the resultant SELF web. In the preferred embodiment shown in FIG. 4, the central waistband panel 34 has four bands 64' of 3 mm width each. There are also three pleats 66' spaced at a width of 6.35 mm. Thus, the central waistband panel has an extension force at 50% extension of about 17 g/cm. The available stretch of the central waistband panel is about 60%. The preferred side panels 36 comprise a SELF web having an equal to or lower extension force and higher available stretch than the central waistband panel 34. The side panels 36 each preferably comprise seven bands 64''' of 3 mm width and six pleats 66''' spaced at a width of 5.6 mm. The side panels thus each have a force/extension characteristic at a 50% extension of about 13 g/cm. The available stretch of each side panel is about 110%. The side panels have different force/extension properties from the central waistband panel, despite the fact that the bands are the same, due to the difference in properties of the base materials and the width of the pleats. (One of the layers of the side panel is the Clopay 1401 polyethylene film while the one of the layers of the central waistband panel is the Tredegar P8863 polyethylene film.) The hip panel 38 comprises a SELF web designed to provide seven bands 64'' of 1 mm width and eight pleats 66'' of 6.35 mm width. The hip panel thus has an extension force at 50% extension of about 3 g/cm. The available stretch of the hip panel is about 60%. Thus, the hip panels preferably have force/extension properties less than the side panels and less than the central waistband panel; however, the amount of extension of the hips panel is greater than the central waistband panel. The extension forces of the hip panel are less than that of the central waistband panel due to the width of the bands.

With the force/extension characteristics providing extension as described above, it has also been found that the positional relationship between certain elements of the extensible back waist feature and/or the diaper further enhance the fit and containment of the diaper.

It has been found that the side panels 36 should be joined to not only the central waistband panel 34 but also to at least a portion of the hip panel 38. This configuration allows forces generated in the side panels by fitting the diaper on the wearer to be transmitted not only through the central waistband panel but also the portion of the hip panel adjacent the central waistband panel. The hip panel thus extends to accommodate forces distributed in the central waistband panel causing less strain and stress on the diaper and expands with the forces in the side panels to better accommodate the hips and buttocks of the wearer while providing additional extensibility to accommodate further movements of the hips and buttocks as the wearer moves, walks, stands, etc. While the side panels may be disposed so as to be longitudinally aligned with the entire hip panel, it is preferred that the side panels are longitudinally aligned with only a portion of the hip panel so that a continuous line of force through the waistband is provided and in order to maximize expansion of the lower back side of the hip panel. It is preferred that the side panel overlap with the hip panels from 10% to about 90%, more preferably from about 40% to about 60% of the length (longitudinal dimension) of the total length of the side panel. In the embodiment shown in FIG. 1, the side panels overlap with the hip panel about 27 mm with the hip panels extending beyond the side panels from about 13 mm to about 43 mm, preferably about 28 mm.

As shown in FIG. 4, the side panel 36 is preferably joined to a nonextensible portion of both the central waistband panel 34 and the hip panel 38. This nonextensible portion, bridging element 58, allows forces generated in the side panels 36 during application and use of the diaper to be "diffused" or spread out to more evenly distribute the forces in the central waistband panel 34 and the hip panel 38. While the side panel 36 could be joined to an extensible portion or be constructed as unitary with the SELF webs of the central waistband panel and the hip panel, such a construction allows direct force transfer through specific sites thereby concentrating the forces and stresses rather than allowing them to be distributed over a wider area. The side panels can be joined to the panels, preferably the bridging element 58, in a number of different ways as are known in the art and previously discussed herein, including by adhesives, heat/ pressure bonds ultrasonic bonding or mechanical bonding. The side panels are preferably bonded to the other panels via mechanical bonding.

It has also been found that the positioning of the operative ends 55 of the leg elastics (elastic strands 54) with respect to the leg edge 37 of the side panel 36 is an important parameter in optimizing fit about the leg of the wearer. While the elastic strands 54 may be any length consistent with providing a leg cuff, it has been found that the operative ends 55 of the elastic strands 54 preferably extend to the leg edge 37 of the side panels 36 to eliminate the possibility of leg gapping and the resultant leakage at the back of the legs. (The term, "operative ends", as used herein means the point where the elastic strand is operatively joined to the leg flap panel and contracts or gathers the leg flap panel. Thus, unadhered segments of the elastic strands may extend beyond the zones defined herein since they do not act on the diaper or perform a contractive or gathering function.)

Leakage and gapping at the back of the legs is improved when the elastic strands 54 extend beyond the waist edge 56 of the absorbent core 28 into the hip panel 38 because the elastic strands tend to curve with the extension of the hip panel and better fit around the buttocks of the wearer. (See FIG. 3.) The position of the operative ends 55 of the elastic strands 54 in the hip panel 38 also couples the leg closure and leg fit with the central waistband panel 34 and side panels 36 to provide a continuous closure and line of force about the legs. Thus, it has been found that the operative ends of the elastic strands should extend to at least the hip panels, preferably into the hip panels, and more preferably to about the leg edge of the side panels, most preferably within about 10 mm in either direction from the leg edge.

The positioning of the absorbent core 28 may also affect the performance of the diaper and the back waist feature. Since the absorbent core is relatively nonextensible, positioning the absorbent core in an extensible feature can degrade the integrity of the core during use, especially when wet, and can restrict the extension of the panel. Thus, as shown in FIG. 1, the absorbent core 28 does not extend into the hip panel 38. However, the absorbent core may extend into the hip panel if more absorbent capacity is needed or a stiffener is required. If the absorbent core extends into the hip panel, it is preferable to either not make that portion of the hip panel extensible or not join that portion of the absorbent core to the extensible panel, thus allowing the absorbent core to "float" and not restrict the extension of the hip panel.

FIG. 3 shows the diaper of FIG. 1 in a flat configuration approximating the forces applied to the extensible back waist feature 32 during wear. As can be seen from the drawing, the side panels 36 extend such that their waist edge 37' is extended more than the leg edge 37 (about 80 mm versus 75 mm) such that more of the forces through the side panels are resolved adjacent the waist edge 37' (the end edge 48 of the diaper 20). The central waistband panel 34 has also been extended (to about 250 mm) with the majority of the forces resolved through the central waistband panel. The hip panel 38 has been extended with more extension adjacent its upper edge than its lower edge. However, this extension allows the hip panel to better wrap the hips and buttocks of the wearer resulting in better fit and improved containment at the hips. The elastic strands 54 of the leg cuffs 30 are shown to curve in the hip panels 38 to provide a cuff that better conforms to the buttocks of the wearer. (It should be noted that if the leg cuff comprises a barrier cuff as is described in the above-referenced U.S. Pat. No. 4,695,278 (Lawson), the barrier cuff will also curve in the same manner and provide better fit about the buttocks.)

As shown in FIG. 1, the diaper 20 may also be provided with an extensible front waist feature 42. The extensible front waist feature 42 is designed to fit around the abdomen in the front waist of the wearer to improve the fit and containment of the diaper at the front waist. The extensible front waist feature 42 is positioned in the front waist panel 43 and extends longitudinally outwardly from the chassis assembly 22, preferably the waist edge 56 of the absorbent core 28, and generally forms at least a portion of the end edge 48 of the diaper 20 in the front waist region 45. The extensible front waist feature 42 may comprise any of the known configurations of an elastic feature or any of the extensible features as described herein. For example, the extensible front waist feature may comprise any of the elasticized waistbands as are known in the art such as are disclosed in the above-referenced U.S. Pat. No. 4,515,595 (Kievit, et al.) and U.S. Pat. No. 5,151,092 (Buell, et al.).

Further, the extensible front waist feature may comprise a stretch laminate such as a zero strain stretch laminate as is described in U.S. Pat. No. 5,151,092 (Buell, et al.). Examples of alternative extensible front waist features are described herein with respect to the alternative embodiments. In an especially preferred embodiment of the present invention as is shown in FIG. 1, the front waist panel 43 comprises a SELF web. The SELF web of the front waist panel preferably has the same or similar force/extension characteristics as the SELF web of any of the other panels of the diaper, including, for example, the central waistband panel, the hip panel, or the side panel. However, the SELF web of the front waist panel may also be designed to have its own unique force/extension characteristics. In a preferred embodiment for a large (8 kg to 14 kg) baby diaper, the front waist panel has a longitudinal dimension of about 15 mm and a lateral dimension of about 180 mm. The extension force of the front waist panel is preferably greater than or equal to the extension force of the central waistband panel. The SELF web of the front waist panel is preferably designed to have three bands of 3 mm width and 2 pleats of 6.35 mm width to provide an extension force at 50% extension of 26 g/cm with an available stretch of 60%.

The diaper 20 is also provided with a closure system for fitting the diaper on the wearer. While the closure system may take on a number of configurations such as adhesive tape tabs, mechanical closure tape tabs, fixed position fasteners, side seams as for training pants, or any other closure means as are known in the art; as shown in FIG. 1, the closure system preferably comprises an adhesive tape tab fastening system including a pair of tape tabs 40 and a landing member, preferably a reinforcing strip 41 as in FIG. 1 or, the alternative, a portion of the backsheet, positioned in the front waist region 45 of the diaper 20. Examples of suitable adhesive tape tab fastening systems are disclosed in U.S. Pat. No. 3,848,594 issued to Buell on Nov. 19, 1974; and U.S. Pat. No. 4,662,875 issued to Hirotsu and Robertson on May 5, 1987; each of which are incorporated herein by reference. Examples of other closure systems, including mechanical closure systems, useful in the present invention, are disclosed in U.S. Pat. No. 4,869,724 issued to Scripps on Sep. 26, 1989; U.S. Pat. No. 4,848,815 issued to Scripps on Jul. 11, 1989; and the two-point fastening system described in U.S. Pat. No. 5,242,436 issued to Weil, Buell, Clear, and Falcone on Sep. 7, 1993; each of which are incorporated herein by reference. When a two-point fastening system is used, the waist closure members of the waist closure system are preferably longitudinally aligned with the extensible front waist feature and laterally aligned with the elastic strands of the extensible leg cuff to provide an effective closure about both the legs and the waist.

In an alternative embodiment of the present invention, the diaper may also be provided with ear flap panels that extend laterally outwardly from the chassis assembly and the front waist panel. The ear flap panels provide a structure to which the waist feature can be attached to encircle the legs and waist of the wearer. The ear flap panels may take on a number of different sizes, shapes, configurations, and materials. The ear flap panels may comprise a portion of the material(s) making up one or more of the diaper elements, including the topsheet and the backsheet. Alternatively, the ear flap panels may comprise a separate element or a plurality of elements affixed to the diaper. Suitable materials for use as the ear flap panels include woven webs; nonwoven webs; films, including polymeric films; foams; laminate materials including film laminates, nonwoven laminates, or zero strain laminates; elastomers; composites; SELF webs;

or any combination of these materials. The ear flap panels may be joined to the chassis assembly by any means as are known in the art; for example, the ear flaps may be continuously or intermittently bonded to the chassis assembly using heated or unheated adhesive, heat bonding, pressure bonding, ultrasonic bonding, dynamic mechanical bonding, or any other method that is known in the art.

The diaper 20 is preferably applied to a wearer by positioning the back waist region 46 under the wearer's back and drawing the remainder of the diaper between the wearer's legs so that the front waist region 45 is positioned across the front of the wearer. The tab portions of the tape tabs 40 are then released from the release portion. The diaperer then wraps the side panel 36 around the wearer, while still grasping the tab portion. The side panel will typically be extended and tensioned during this operation so as to conform to the size and shape of the wearer. The tape tab 40 is secured to the reinforcing strip 41, the landing member, on the chassis assembly 22 to effect a side closure. The process is then repeated with the other tape tab. Thus, the diaper is closed on the wearer and the extensible back waist feature and the other elements, if provided, provide the fit and containment benefits as described herein.

Alternatively, the diaper may be provided with a closure system that allows the side panels to be first joined together. The diaperer then brings the chassis assembly between the legs of the wearer and joins the chassis assembly to the outer layer of the waist feature. Such a configuration and securing method is more fully described in the above-referenced U.S. application Ser. No. 08/044,562 (New, et al.).

Figure 16:
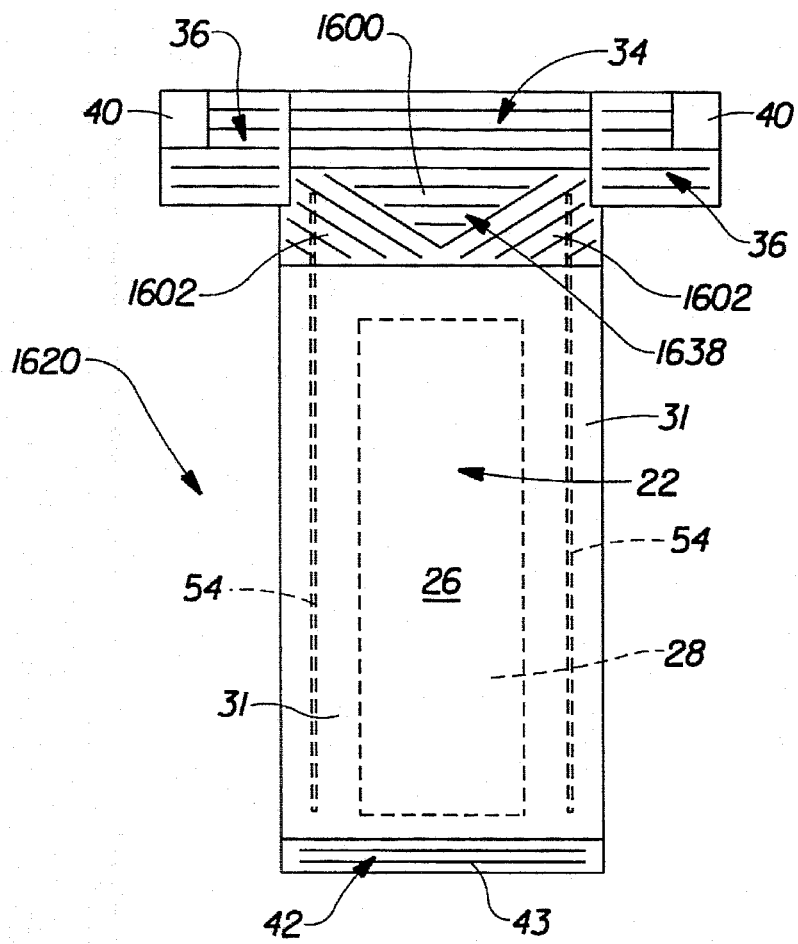
FIG. 16 is a simplified plan view of an alternative disposable diaper embodiment of the present invention generally showing the direction of extensibillity of the panels of the extensible back waist region.

FIG. 16 is a simplified plan view of an alternative disposable diaper 1620 of the present invention wherein the hip panel 1638 has a multiple zone SELF web construction. (The particular construction of the SELF web has been simplified by showing the bands making up the SELF web.) The hip panel 1638 has three zones: a central zone 1600 and two leg zones 1602. The SELF web of each leg zone 1602 preferably has the first and second regions disposed at an angle to the lateral direction so that extensibility is provided at an angle to the lateral direction. Lateral forces developed in the side panels 36 are directed along a line at an angle to the lateral direction through the hip panels 1638 to more conformably fit about the buttocks of the wearer. The SELF web of the central zone 1600 is similar to the SELF web pattern of the hip panel 38 shown in FIG. 1. The central zone 1600 provides lateral extensibility adjacent the central waistband panel 34. In the embodiment shown in FIG. 16, the central zone 1600 has a higher extension force than the leg zones 1602 (lower extension/available stretch), preferably even high than the central waistband panel 34, to provide a snug fit by holding the diaper in place without roll-over or "pooching" out. The central zone 1600 may even provide no extensibility (i.e., nonextensible), if desired.

It is preferred, however, that in some embodiments, that the extension forces of the central zone be less than or equal to the lateral vector component of the extension forces of the leg zones, particularly when a barrier cuff is used for the leg cuff.) This configuration of the hip panel better distributes forces in both the legs and the buttocks region by allowing extensibility both in the lateral and longitudinal direction in the leg zone. When the leg cuff of the diaper comprises a barrier cuff such as is described in U.S. Pat. No. 4,695,278 (Lawson), the hip panel may also comprise a central zone and a pair of leg zones. The side edges of the central zone are positioned inward from the proximal edges of the barrier cuffs. Such a proximal edge is positioned in each leg zone. The extension force of the central zone is preferably less than the extension force of the leg zone to anchor each barrier cuff while providing extensibility for the hip panel.

Figure 17:
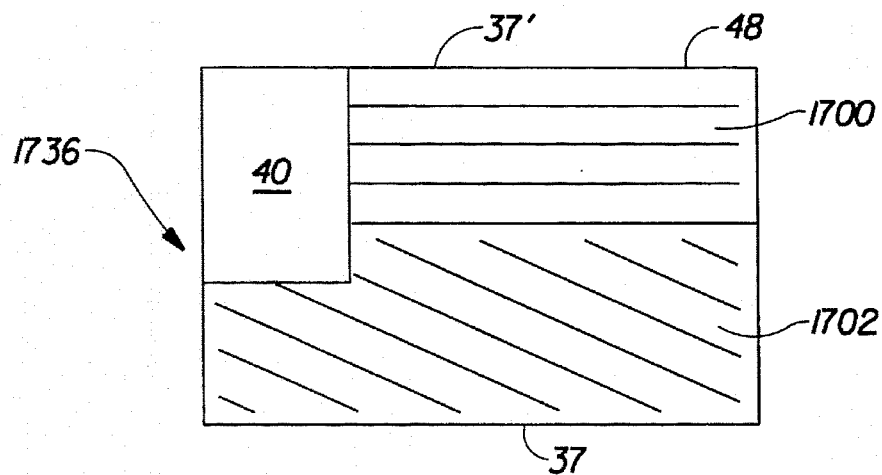
FIG. 17 is a simplified close up plan view of an alternative configuration of the side panel of the disposable diaper embodiment of the present invention.

FIG. 17 shows an alternative embodiment of a side panel 1736 of the back waist feature 32 wherein the side panel 1736 has a multiple zone SELF web construction. The portion of the side panel 1736 adjacent the end edge 48 of the diaper and in alignment with the central waistband panel 34, the waist zone 1700, comprises a first SELF web that provides distribution of the extension forces and extension in a first direction having a vector component in the lateral direction, preferably the lateral direction. The side panels 1736 also have a leg zone 1702 adjacent the leg edge 37 of the side panel 1736 that comprises a second SELF web having a pattern of bands and pleats providing force resolution and extensibility in a second direction different from the first direction, preferably at an angle to the lateral direction. This second direction of extension provides better fit about the wearer by distributing the forces at an angle in the leg zone 1702. It should also be noted that while the embodiment of FIG. 17 shows the side panel as one continuous member, the side panel can also be constructed from two separate SELF webs joined together to form a two by two side panel such as is disclosed in the above-referenced U.S. patent application Ser. No. 08/155,048 (Robles, et al.), hereby incorporated herein by reference.

Figure 18:
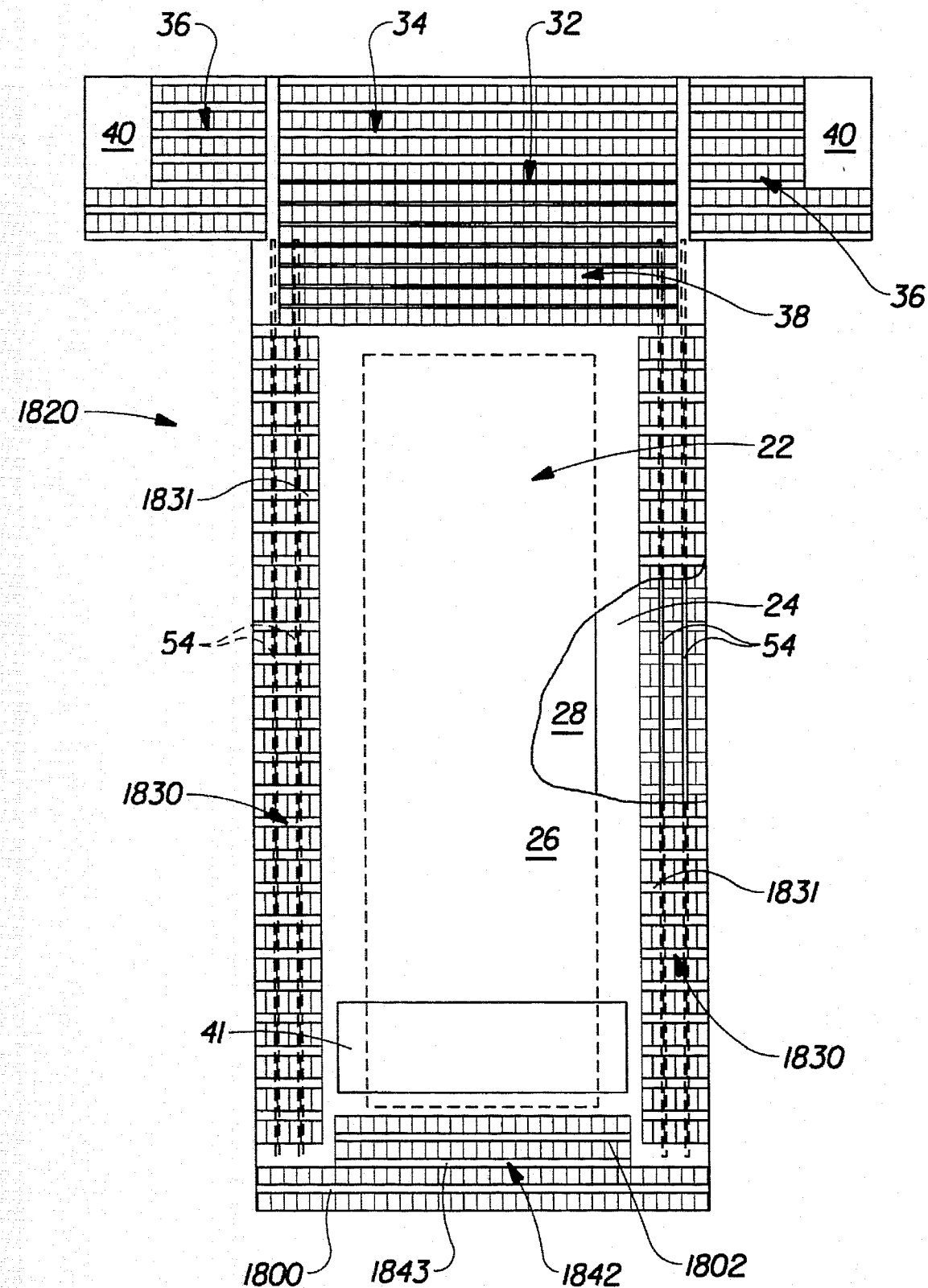
FIG. 18 is a plan view of a still alternative disposable diaper embodiment of the present invention.

FIG. 18 shows an alternative disposable diaper 1820 of the present invention wherein the leg flap panels 1831 further comprise a SELF web and the front waistband panel 1842 is a multiple zone SELF web. The SELF web of the leg flap panels provides extensibility in the lateral direction. By providing a SELF web leg cuff next to, over, or outside of the elastic strands 54, the diaper 1820 has an area adjacent the legs which can expand when needed for additional void volume due to heavy loading, and also to provide a snug fit to reduce the possibility of leakage in the leg regions due to gapping. As the diaper is loaded and gets heavier, the weight forces cause the extensible leg flap panels 1831 to expand in the lateral direction thereby reducing gapping at the legs due to this expansion instead of the cuff being pulled downward by the weight and gapping away from the leg. The result is that action of the leg cuff 30 is independent from the absorbent core 28 thus providing better fit and containment. Additionally, the SELF web enhances the softness of the product in the leg cuff and contributes to overall baby friendly aesthetics. In fact, the entire diaper, including the chassis panel 22, may, if desired, comprise a SELF web to provide softness and containment characteristics. In the embodiment shown in FIG. 18, the SELF web of the leg flap panels 1831 has 75 bands of 1 mm width and 74 pleats of 6.35 mm width each. The leg flap panel thus has an extension force at 50% extension of 6 g/cm and an available stretch of 60%. The elastic strands 54 are operatively joined in the leg flap panel to provide an extension force of 60 g at 85% extension. (It has been found that the SELF web should preferably have an extension force no greater than ½ of; preferably between about ⅕ to about ¹/₁₀ of, the extension force of the elastic strands 54. Since the elastic strands 54 are preferably operatively joined to the leg flap panel 1831 to provide an extension force between about 50 and about 60 g, then the extension forces of the leg flap panels are preferably less than 30 g/cm, more preferably less than 20 g/cm, and most preferably less than 10 g/cm, at 50% extension. These extension force characteristics provide the improvements in gapping and containment described herein.

The front waist panel 1832 has multiple zones: a central waistband zone 1800 and a tummy zone 1802. The central waistband zone 1800 provides the function of the front waist feature as previously described herein. The tummy zone 1802 provides extension about the belly of the wearer which typically expands and contracts during use. Thus, the tummy zone 1802 moves with the stomach of the wearer and reduces the tendency of the front waist to sag and gap during use. The extension forces of the overall front waist panel 1843 are preferably less than the extension force of the central waistband panel 34 of the back waist feature 32 to allow the front to "flair" out. The extension force of the front waist panel 1843 is preferably between about 5 g/cm and 15 g/cm at 50% extension. In an alternative embodiment, the extension force of the tummy zone 1802 may be less than or equal to the extension force of the central waistband zone 1800 to allow more extension in the tummy panel to accommodate the wearer's stomach and to provide a line of tension in the central waistband zone that more snugly fits the wearer. (In an alternative embodiment, this diaper may also be provided with the two point fastening system described in U.S. Pat. No. 5,242,436 (Weil, et al.) to further enhance the fit of the diaper.)

Figure 19:
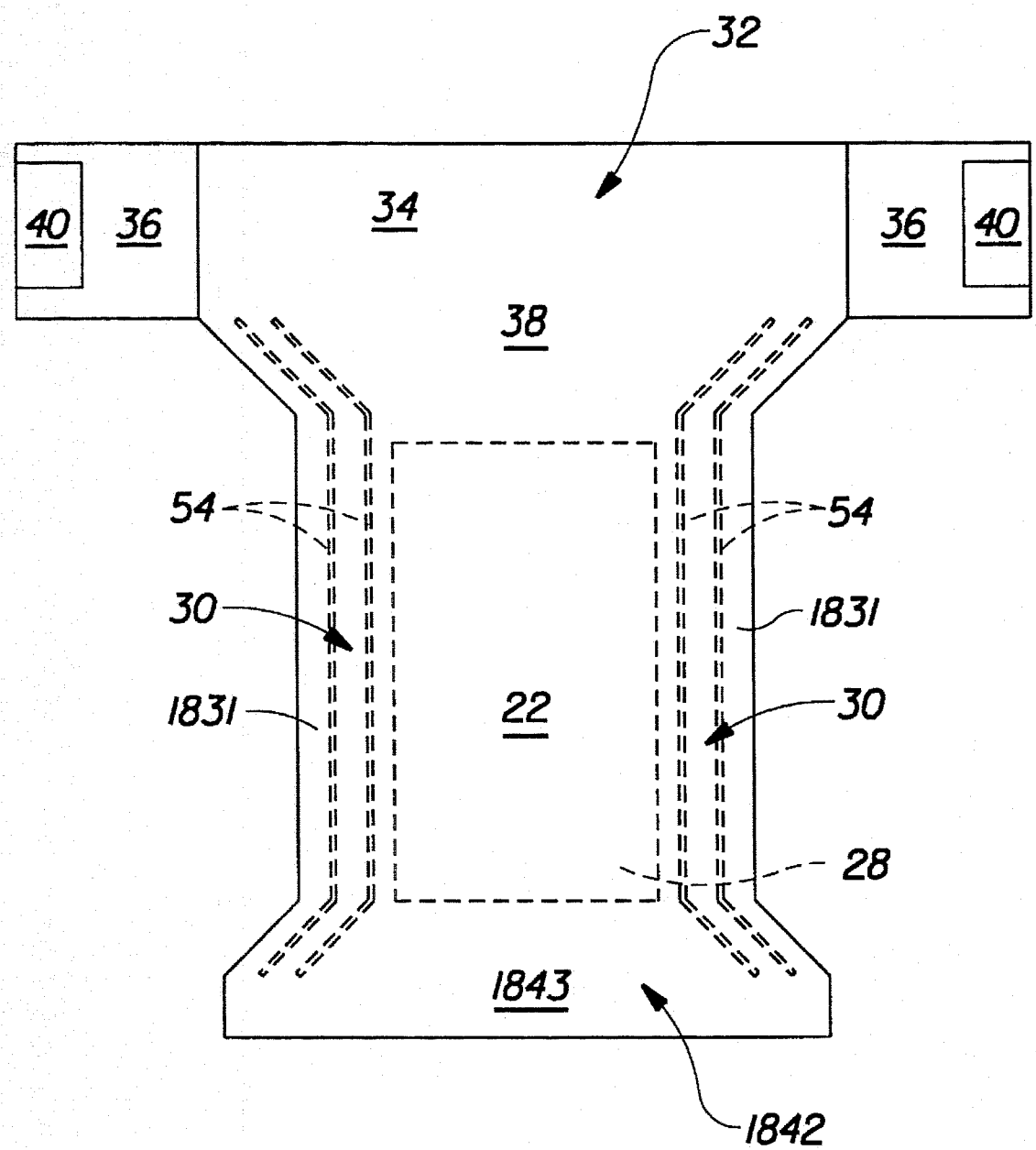
FIG. 19 is a plan view of the alternative disposable diaper embodiment of FIG. 18 showing the diaper in its stretched condition when forces are applied to the side panels and to the front waist feature.

FIG. 19 shows the diaper of FIG. 18 in a flat configuration approximating the forces applied during wear. As can be seen from the drawing, the extensible back waist feature 32 extends in the same manner as described with respect to FIG. 3. However, due to the extensibility of the leg flap panels 1831 and the greater extensibility of the from waist panel 1843, the front waist region of the diaper also tends to flare out. Thus, the diaper 1820 provides an hourglass shape-type fit without the added and the wasted material required for an hourglass shaped diaper. The elastic strands 54 of the leg cuffs 30 are shown to curve in the front waist to provide a cuff that better conforms to the upper thighs of the wearer. In effect, curved elasticization is achieved with a rectangular diaper. (It should be noted that if the leg cuff comprises a barrier cuff as is described in the above-referenced U.S. Pat. No. 4,695,278 (Lawson), the barrier cuff will also curve and provide better fit.)

Figure 20:
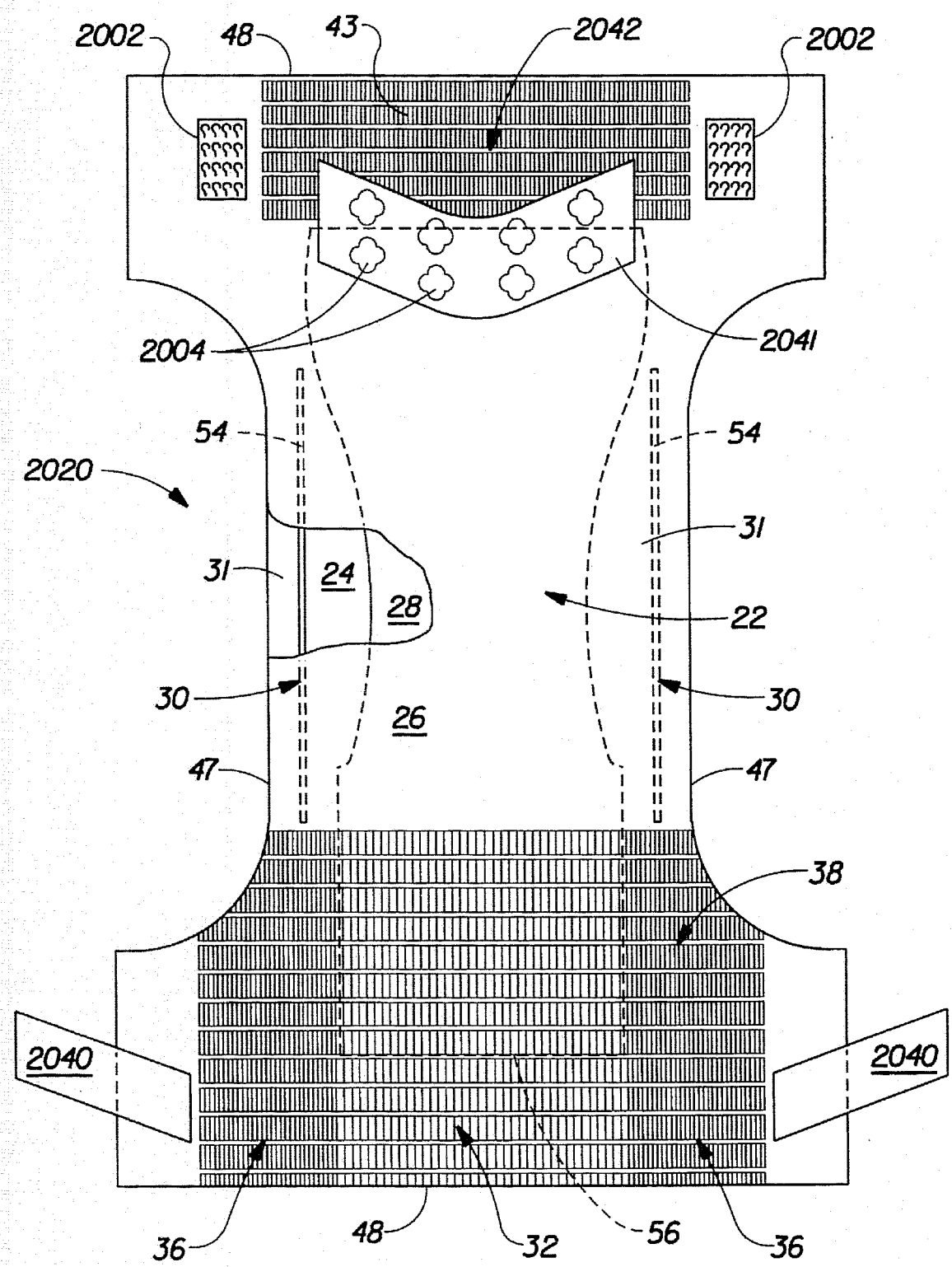
FIG. 20 is a partially cut-away plan view of an alternative disposable diaper embodiment of the present invention having an hourglass shape and an extensible front waist feature of a SELF web.

FIG. 20 shows an alternative embodiment of a diaper 2020 of the present invention. The diaper 2020 has a generally hourglass shape rather than the T-shape previously discussed. The hourglass shape has a leg cutout in the crotch region of the diaper to provide fit about the legs. The extensible back waist feature 32 is similar to the extensible back waist feature described with respect to the T-diaper except for the shape of each panel. Further, in this embodiment, the absorbent core 28 extends into a portion of the hip panel 38. In an especially preferred embodiment, the absorbent core 28 is not joined to the hip panel 38 such that it is allowed to "float" in the hip panel 38. The absorbent core thus provides stiffness in a portion of the hip panel to prevent bunching of the hip panel. The extensible front waist feature 2042 preferably has a pentagon shape such as is described in U.S. Pat. No. 5,151,092 (Buell, et al.). In the embodiment shown in FIG. 20, the extensible front waist feature 2042 comprises a SELF web of the present invention wherein the extensibility of the SELF web is in a pentagon shape due to the nonextensible chevron-shaped landing member, reinforcing strip 2041, being joined over a portion of the SELF web. The closure system for the diaper is preferably the dual tension fastening system described hereinafter providing an angled line of tension about the wearer. The dual tension fastening system comprise a primary fastening system and preferably a waist closure system. As shown in FIG. 20, the tape tabs 2040 of the primary fastening system are disposed at an angle to the lateral direction to provide such an angled line of fastening. The diaper 2020 is also provided with a waist closure system including a pair of first attachment components 2002 longitudinally aligned with the extensible front waist feature 2042 to provide tension through the extensible front waist feature and a second attachment component (not shown) comprising a portion of the topsheet 24.

The closure system anchors the diaper about the wearer throughout the diapers use so the diaper has a reduced likelihood to sag/gap and slide/slip during use. The closure system is designed to create a line or zone of tension causing a hoop force connecting the lumbar curve of the back over the hips to under the abdominal crease to form the anchoring function. This line or lines (zone) of tension (hereinafter, the primary line of tension) is disposed substantially about the perimeter of the low motion zone of the wearer to impart anchoring forces that maintain the position of the diaper throughout wearing. The primary line of tension is preferably disposed at an angle to the horizontal on the body of the wearer (at an angle to the lateral direction of the diaper) such that the primary line of tension extends from around the lumbar curve (the small of the back) over the iliac crest of the hips to the front of the wearer, preferably below the line of the abdominal crease. Thus, the primary line of tension is disposed in the zone of minimal changing body dimension, a sustained wearing position (i.e., the primary line of tension is not disposed over the abdomen of the gluteus maximus which increase and decrease in dimension during movement), such that the primary line of tension stabilizes and maintains anchoring forces which maintaining the position of the diaper on the wearer such that diaper is unlikely to slide or slip downward during the entire time of use due to the movement of the wearer or to the force of the increased weight of the diaper when it is loaded. The angled primary line of tension created by the closure system also imparts an upward anchoring force on the diaper tending to pull the diaper up on the body, and thus counteract the weight force of the loaded diaper, since the primary line of tension has a vector component in the longitudinal direction. The normal anchoring force is created by the primary line of tension (another vector component of the angled primary line of tension) anchoring the diaper, particularly the absorbent core, in the low motion zone since the normal anchoring forces act compressively to push the absorbent core toward the body. These normal anchoring forces thus assist in maintaining the fit of the diaper as well as reducing leakage since the absorbent core is maintained in close relationship with the body. The angled primary line of tension also tends to reduce red marking since the anchoring forces are disposed in the low motion zone such that the body dimension is not increasing or decreasing along the primary line of tension which could cause red marking.

Since the primary line of tension is to be disposed at an angle to the lateral direction to provide its anchoring function, the closure system is designed to provide an angled closure mechanism to insure such a primary line of tension is imparted to the diaper. The closure system may thus comprise a number of different fastening systems for providing an angled primary line of tension. For example, the closure system may simply comprise a primary fastening system. The closure system may additionally anchor a portion of the extensible front waist feature, and, if desired, a portion of the leg cuff.

For the closure system shown in FIG. 20, each securement member of the closure system preferably comprises a tape tab 2040 capable of being secured to a landing member, preferably reinforcing strip 2041, so as to provide a primary line of tension through the diaper at an angle to the lateral direction. Thus, the tape tab is generally shaped and oriented to allow the tape tab to engage the landing member so as to provide a primary line of tension at an angle to the lateral direction, preferably through the diaper substantially about the low motion zone. In the embodiment shown in FIG. 20, the tape tab 2040 is joined to the side panel 36 at an angle to the lateral direction to provide the angled primary tension line desired. For example, a rectangular tape tab such as known in the art or a tape tab having any other shape may be rotated with respect to the lateral direction when applied to the diaper such that the tape tab is disposed at an angle to the lateral direction of preferably between about 5° to about 30°, preferably from about 15° to about 20°.

An alternative embodiment of the tape tab may have the tab portion shaped and oriented at an angle to the lateral direction to insure the formation of the primary line of tension at an angle to the lateral direction. Most preferably, the sidelong edges of the tape tabs are curved to allow angled taping in order to follow the shape/build of the wearer, to create the angled primary line of tension about the low motion zone to anchor the diaper on the wearer, and to allow the diaperer to conveniently apply the tab portion on the landing member so as to accommodate the diaper design. Further, the curved shape of the sidelong edges of the tab portion allows high tape placement in the back waist region yet allows low tape placement on the landing member to minimize marking of the stomach, hips and legs of the wearer to improve the comfort of the diaper for the wearer. The tab portion also accommodates the leg of the wearer in that if the tape tab was positioned too low on the product, marking could occur on the legs of the wearer which would negatively impact comfort and fit. An example of such a tape tab design is disclosed in U.S. patent application Ser. No. 08/072,300, "Absorbent Articles Providing Sustained Dynamic Fit" filed by LaVon, et al. on Jun. 3, 1993, which patent application is incorporated herein by reference.

The landing member can also assume varying sizes and shapes to provide the angled primary line of tension. In a preferred embodiment as illustrated in FIG. 20, the landing member comprises a reinforcing strip 2041 having a chevron shape so as to create the angled primary line of tension of the present invention. The reinforcing strip 2041 is also preferably provided with indicia means 2004 for aiding the diaper and fitting the diaper to a wearer to obtain optimal waist fit and leg opening fit. The indicia means 2004 are preferably disposed in rows disposed at an angle to the lateral direction, preferably at the same angle as the tape tabs 2040, to allow angled fastening of the tape tab for optimized fit and for providing an angled primary line of tension. (In an alternative configuration, the landing member can be extensible, for example—formed from a SELF web comprising a nonwoven material, to allow the front waist region to expand even more to accommodate the growth of the wearer's stomach.)

As shown in FIG. 20, the closure system preferably additionally comprises a waist closure system that anchors a span of the front waist panel 43, preferably the extensible front waist feature 2042. Such a waist closure system is disclosed in the above-referenced U.S. patent application Ser. No. 08/072,300 (LaVon, et al.) and U.S. Pat. No. 5,242,436 (Weil, et al.). Alternatively, the components of the waist closure system can also be configured to provide an angled line of tension (e.g., the first attachment components may be joined at an angle to the lateral direction).

Figure 21:
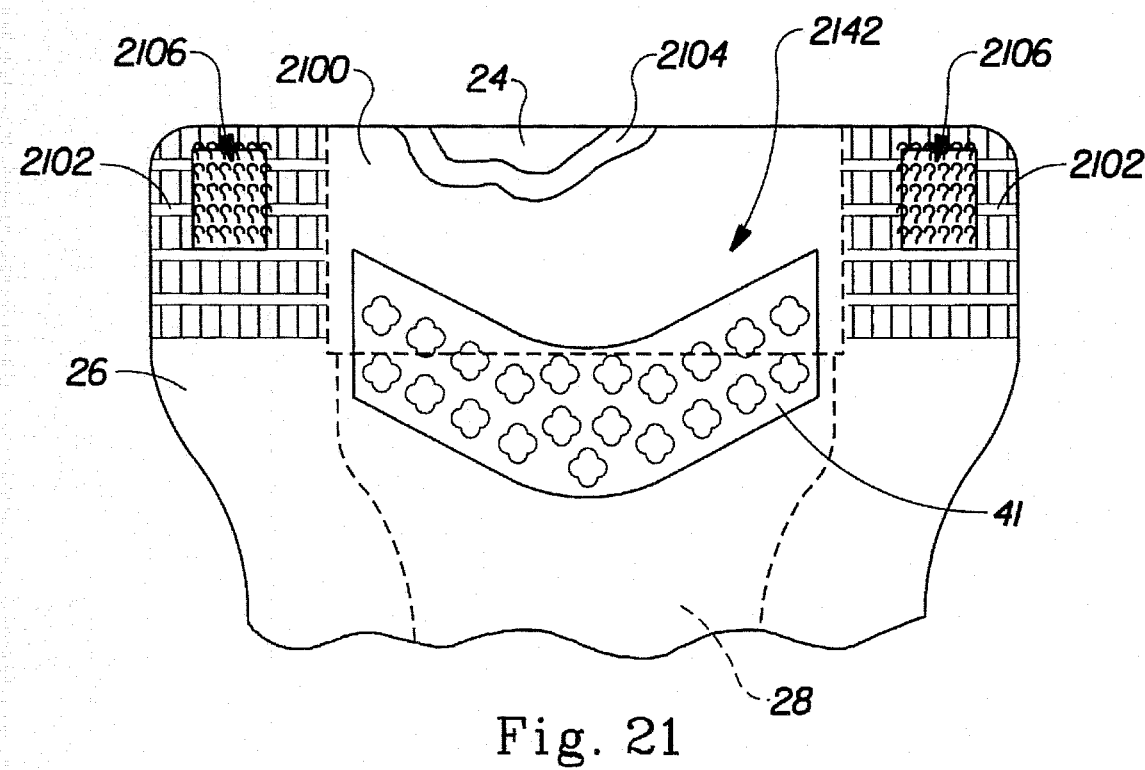
FIG. 21 is a fragmentary plan view of an alternative extensible front waist feature of the present invention.

FIG. 21 shows a further alternative embodiment of an extensible front waist feature 2142 of the present invention. The front waist panel 2143 has a central waistband panel 2100 and a pair of ear panels 2102 disposed on either lateral side of the central waistband panel 2100. The central waistband panel 2100 preferably comprises a stretch laminate, more preferably a zero strain stretch laminate, such as are described in above-referenced U.S. Pat. No. 5,151,092. The central waistband panel 2100 thus comprises a portion of the topsheet 24, a portion of the backsheet 26, and an elastomeric member 2104 positioned between the topsheet 24 and the backsheet 26, all of which have been mechanically stretched. (It should be noted that the central waistband panel has also been passed through the SELF process; however, the bands and pleats have not been shown in the drawing for simplicity purposes.) The ear panels 2102 each comprise a SELF web to further enhance the stretchability and extensibility of the extensible front waist feature 2142. Each ear panel SELF web is similar to the SELF webs described with respect to use for any of the panels of the back waist feature 32. This provides ease of manufacture since the ear panel SELF webs can be formed simultaneously with the central waistband panel 34 of the extensible back waist feature 32 of the previous diaper during continuous manufacture. Further, for ease of manufacture, the central waistband panel 34 of the back waist feature 32 may alternatively comprise a stretch laminate, preferably a zero strain stretch laminate, so that the same piece of elastic material may form the elastomeric member forming both central waistband panels. The primary fastening system of the closure system comprises a landing member comprising a reinforcing strip 2041 having a chevron shape. The closure system additionally comprises a waist closure system, including the first attachment components 2106, for providing tension through the extensible front waist feature 2142.

Figure 22:
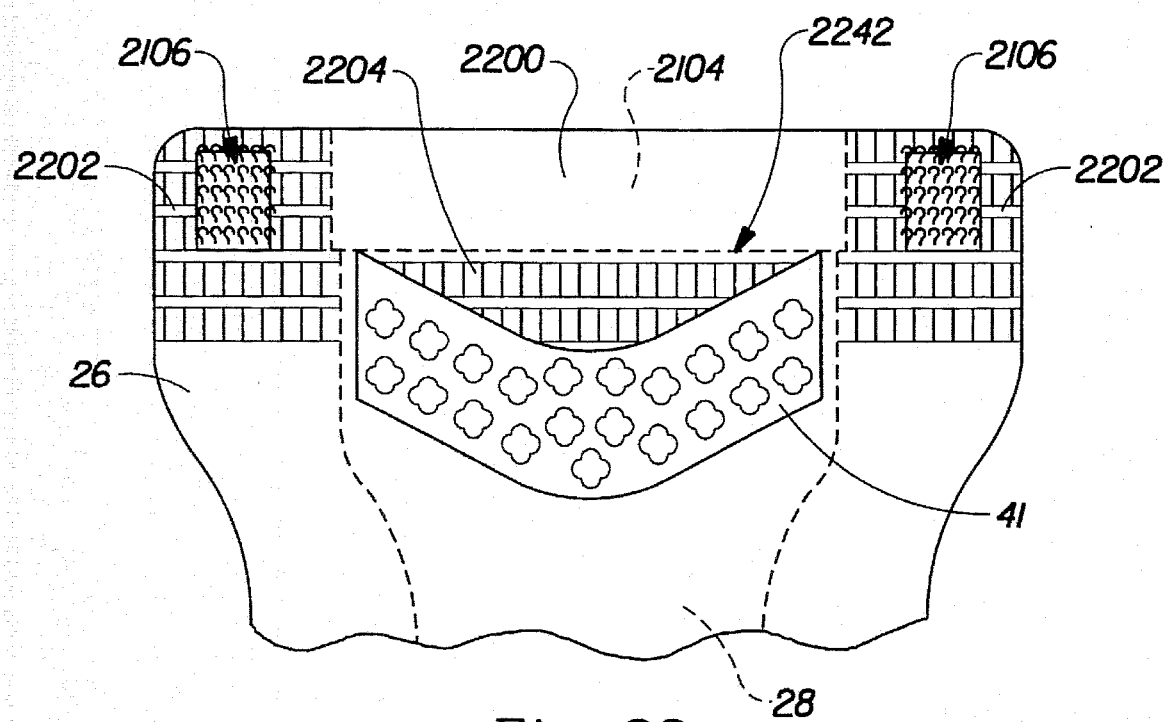
FIG. 22 is a fragmentary plan view of a further alternative extensible front waist feature of the present invention.

FIG. 22 shows a further alternative embodiment of an extensible front waist feature 2242 of the present invention. The front waist panel 2243 comprises a central waistband panel 2200, a tummy panel 2204, and a pair of ear panels 2202. The central waistband panel 2200 is preferably a zero strain stretch laminate as described herein with respect to FIG. 21. The ear panels 2202 are also similar to the ear panels 2102 shown in FIG. 21. The tummy panel 2204 extends longitudinally inwardly from the central waistband panel 2200 and comprises a SELF web. The SELF web of the tummy panel 2204 can be the same or similar to the SELF web of the ear panels or it can have less extension forces than the ear panels.

Figure 23:
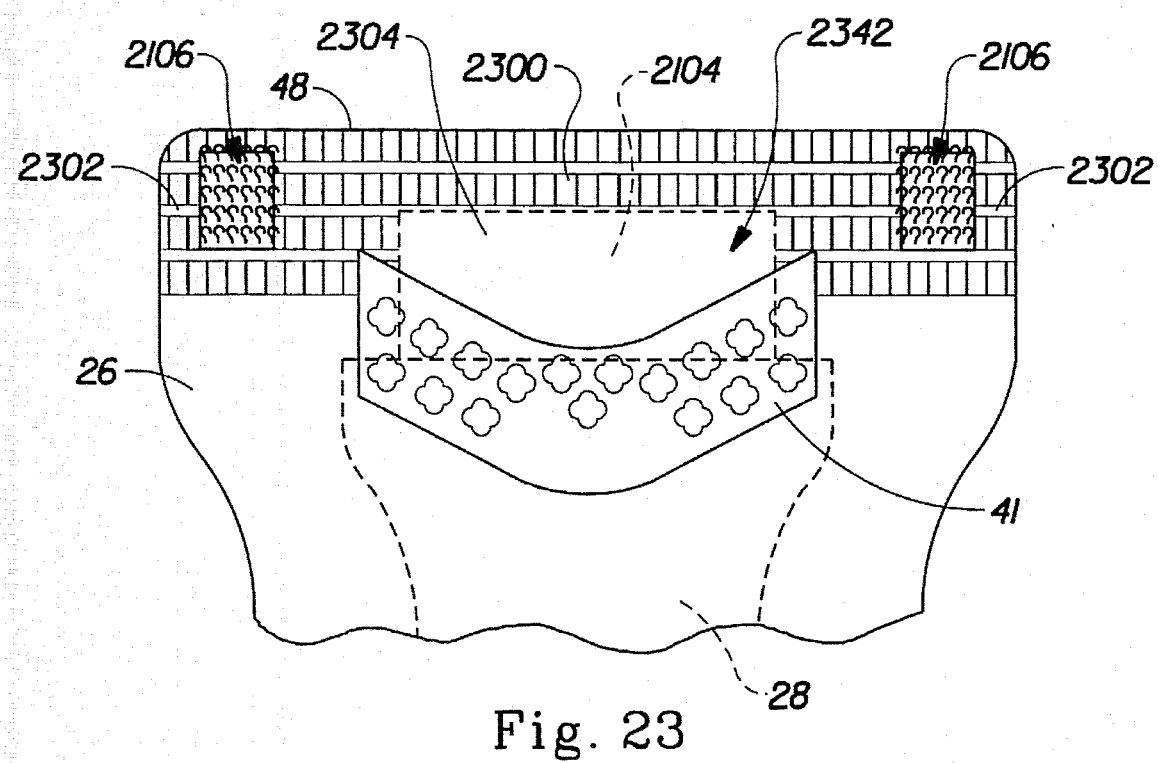
FIG. 23 is a fragmentary plan view of a still further alternative extensible front waist feature of the present invention.

FIG. 23 shows another alternative embodiment of an extensible front waist feature 2342 of the present invention. The front waist panel 2343 comprises a central waistband panel 2300, a tummy panel 2304, and a pair of ear panels 2302 on either longitudinal side of the central waistband panel 2300. In this embodiment, the tummy panel 2304 comprises a stretch laminate, preferably a zero strain stretch laminate, comprising an elastomeric member 2104. The central waistband panel 2300 and the ear panels 2302 each preferably comprise a SELF web. The central waistband panel 2300 extends longitudinally inwardly from the end edge 48 from about 6 mm to about 25 mm, preferably about 12 mm. The force/extension properties of each SELF web may be the same or be different depending upon the desired extensibility of each panel. In the embodiment shown in FIG. 23, each of the SELF webs preferably has the same extension force properties. This front waist feature 2342 thus has a "SELF window." This front waist feature thus reduces sagging since there is no elastic adjacent the end edges to pull down the waist. (In an alternative embodiment of this configuration, the extensible back waist feature may have arcuate shape or angled to the lateral direction bands and pleats for the SELF webs to provide force resolution and extensibility at an angle to the lateral direction.

Figure 24:
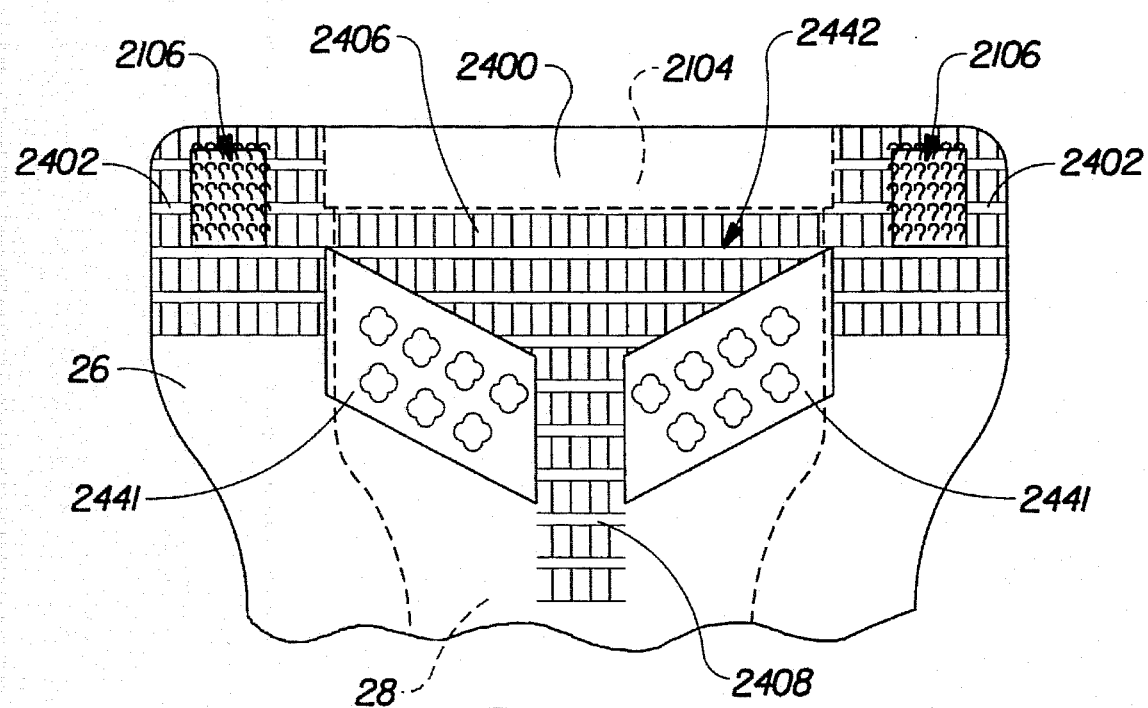
FIG. 24 is a fragmentary plan view of an even still further alternative extensible front waist feature of the present invention.

FIG. 24 shows a further alternative embodiment of an extensible front waist feature 2442 of the present invention. The front waist panel 2443 comprises a central waistband panel 2400, a pair of ear panels 2402, a tummy panel 2406, and a landing panel 2408. The central waistband panel 2400 comprises a stretch laminate, preferably a zero strain stretch laminate comprising an elastomeric member 2104. The ear panels 2402, the tummy panel 2406, and the landing panel 2408 each comprise a SELF web. The landing panel 2408 extends longitudinally inwardly from and preferably beyond the landing member of the primary fastening system. As shown in FIG. 24, the landing member comprises a pair of reinforcing strips 2441 laterally spaced from each other and positioned on the diaper at an angle to the lateral direction. The landing panel SELF web is laterally bounded by the reinforcing strips 2441 to provide stretch and extensibility between the reinforcing strips 2441.

TEST METHODS

Surface-Pathlength

Pathlength measurements of formed material regions are to be determined by selecting and preparing representative samples of each distinct region and analyzing these samples by means of microscopic image analysis methods.

Samples are to be selected so as to be representative of each region's surface geometry. Generally, the transition regions should be avoided since they would normally contain features of both the first and second regions. The sample to be measured is cut and separated from the region of interest. The "measured edge" is to be cut parallel to a specified axis of elongation interest. Usually this axis is parallel to the formed primary-axis of either the first region or the second region. An unstrained sample length of one-half inch is to be "gauge marked" perpendicular to the "measured edge" while attached to the web material, and then accurately cut and removed from the web material.

Measurement samples are then mounted onto the long-edge of a microscopic glass slide. The "measured edge" is to extend slightly (approximately 1 mm) outward from the slide edge. A thin layer of pressure-sensitive adhesive is applied to the glass face-edge to provide a suitable sample support means. For highly formed sample regions it has been found desirable to gently extend the sample in its axial direction (without imposing significant force) simultaneous to facilitate contact and attachment of the sample to the slide-edge. This allows improved edge identification during image analysis and avoids possible "crumpled" edge portions that require additional interpretation analysis.

Images of each sample are to be obtained as "measured edge" views taken with the support slide "edge on" using suitable microscopic measuring means of sufficient quality and magnification. Data herein presented was obtained using the following equipment; Keyence VH-6100 (20× Lens) video unit, with video-image prints made with a Sony Video printer Mavigraph unit. Video prints were image-scanned with a Hewlett Packard ScanJet IIP scanner. Image analysis was on a Macintosh IICi computer utilizing the software NIH MAC Image version 1.45.

Using this equipment, a calibration image initially taken of a grid scale length of 0.500" with 0.005" increment-marks to be used for calibration setting of the computer image analysis program. All samples to be measured are then video-imaged and video-image printed. Next, all video-prints are image-scanned at 100 dpi (256-level gray scale) into a suitable Mac image-file format. Finally, each image-file (including calibration file) is analyzed utilizing Mac Image 1.45 computer program. All samples are measured with freehand line-measurement tool selected. Samples are measured on both side-edges and the lengths recorded. Simple film-like (thin & constant thickness) samples require only one end-edge to be measured. Laminate and thick foam samples are measured on both side-edges. Length measurement tracings are to be made along the full gage length of cut sample. In cases of highly deformed samples, multiple (partially overlapping) images may be required to cover the entire cut sample. In these cases, select characteristic features common to both overlapping-images and utilize as "markers" to permit image length readings to adjoin but not overlap.

The final determination of surface-pathlength for each region is obtained by averaging the lengths of five (5) separate ½" gage-samples of each region. Each gage-sample "surface-pathlength" is to be the average of both side-edge surface pathlengths.

Poisson's Lateral Contraction Effect

The Poisson's lateral contraction effect is measured on an Instron Model 1122, as available from Instron Corporation of Canton, Mass., which is interfaced to a Gateway 2000 486/33 Hz computer available from Gateway 2000 of N. Sioux City, S. Dak., using Test Works™ software which is available from Sintech, Inc. of Research Triangle Park, N.C. All essential parameters needed for testing are input in the TestWorks™ software for each test. Data collection is accomplished through a combination of manual sample width measurements, and elongation measurements made within TestWorks™.

The samples used for this test are 1" wide×4" long with the long axis of the sample cut parallel to the direction of the first region of the sample. The sample should be cut with a sharp knife or suitably sharp cutting device designed to cut a precise 1" wide sample. It is important that a "representative sample" should be cut so that an area representative of the symmetry of the overall pattern of the deformed region is represented. There will be cases (due to variations in either the size of the deformed portion or the relative geometries of regions 1 and 2) in which it will be necessary to cut either larger or smaller samples than is suggested herein. In this case, it is very important to note (along with any data reported) the size of the sample, which area of the deformed region it was taken from and preferably include a schematic of the representative area used for the sample. In general, an "aspect ratio" of (2:1) for the actual extended tensile portion (1l:w1) is to be maintained if possible. Five samples are tested.

The grips of the Instron consist of air actuated grips designed to concentrate the entire gripping force along a single line perpendicular to the direction of testing elongation having one flat surface and an opposing face from which protrudes a half round. No slippage should be permitted between the sample and the grips. The distance between the lines of gripping force should be 2" as measured by a steel rule held beside the grips. This distance will be referred to from here on as the "gauge length".

The sample is mounted in the grips with its long axis perpendicular to the direction of applied elongation. An area representative of the overall pattern geometry should be symmetrically centered between the grips. The crosshead speed is set to 10 in/min. The crosshead moves to the specified strain (measurements are made at both 20 and 60% elongation). The width of the sample at its narrowest point (w2) is measured to be the nearest 0.02" using a steel rule. The elongation in the direction of applied extension is recorded to the nearest 0.02" on the TestWorks software. The Poisson's Lateral Contraction Effect (PLCE) is calculated using the following formula:

$$PLCE = \frac{\frac{W2-W1}{W1}}{\frac{l2-l1}{l2}}$$

where $w_2$=The width of the sample under an applied longitudinal elongation;

$w_1$=The original width of the sample;

$l_2$=The length of the sample under an applied longitudinal elongation; and $l_1$=The original length of the sample (gauge length);

Measurements are made at both 20 and 60% elongation using five different samples for each given elongation. The PLCE at a given percent elongation is the average of five measurements.

Hysteresis Test

The hysteresis test is used for measuring the percent set and percent force relaxation of a material. The tests are performed on an Instron Model 1122, available from Instron Corporation of Canton, Mass. which is interfaced to a Gateway 2000 486/33 Hz computer available from Gateway 2000 of N. Sioux City, S. Dak. 57049, using TestWorks™ software which is available from Sintech, Inc. of Research Triangle Park, N.C. 27709. All essential parameters needed for testing are input in the TestWorks™ software for each test (i.e., Crosshead Speed, Maximum percent elongation Point and Hold Times). Also, all data collection, data analysis and graphing are done using the TestWorks™ software.

The samples used for this test are 1" wide×4" long with the long axis of the sample cut parallel to the direction of maximum extensibility of the sample. The sample should be cut with a sharp exacto knife or some suitably sharp cutting device design to cut a precise 1" wide sample. (If there is more than one direction of elongation of the material, samples should be taken parallel to representative directions of elongation.) The sample should be cut so that an area representative of the symmetry of the overall pattern of the deformed region is represented. There will be cases (due to variations in either the size of the deformed portion or the relative geometries of the first and second regions) in which it will be necessary to cut either larger or smaller samples than is suggested herein. In this case, it is very important to note (along with any data reported) the size of the sample, which area of the deformed region it was taken from and preferably include a schematic of the representative area used for the sample. Three separate tests at 20, 60 and 100% strain are typically measured for each material. Three samples of a given material are tested at each percent elongation.

The grips of the Instron consist of air actuated grips designed to concentrate the entire gripping force along a single line perpendicular to the direction of testing stress having one flat surface and an opposing face from which protrudes a half round to minimize slippage of the sample. The distance between the lines of gripping force should be 2" as measured by a steel rule held beside the grips. This distance will be referred to from hereon as the "gauge length". The sample is mounted in the grips with its long axis perpendicular to the direction of applied percent elongation. The crosshead speed is set to 10 in/min. The crosshead moves to the specified maximum percent elongation and holds the sample at this percent elongation for 30 seconds. After the thirty seconds the crosshead returns to its original position (0% elongation) and remains in this position for 60 seconds. The crosshead then returns to the same maximum percent elongation as was used in the first cycle, holds for thirty seconds and then again returns to zero.

A graph of two cycles is generated. A representative graph is shown in FIG. 7. The percent force relaxation is determined by the following calculation of the force date from the first cycle:

$$\frac{\text{Force at Max. \% elongation} - \text{Force after 30 sec. hold}}{\text{Force at Maximum \% elongation (cycle 1)}} \times 100 = \text{\% Force Relaxation}$$

The percent set is the percent elongation of the sample of the second cycle where the sample starts to resist the elongation. The percent set and the percent force relaxation are shown graphically also in FIGS. 7 and 15. The average percent force relaxation and percent set for three samples is reported for each maximum percent elongation value tested.

Tensile Test

The tensile test is used for measuring extension force (force) versus percent elongation properties and percent available stretch of a material. The tests are performed on an Instron Model 1122, available from Instron Corporation of Canton, Mass. which is interfaced to a Gateway 2000 486/33 Hz computer available from Gateway 2000 of N. Sioux City, S. Dak., using TestWorks™ software which is available from Sintech, Inc. of Research Triangle Park, N.C. All essential parameters needed for testing are input in the TestWorks™ software for each test. Also, all data collection, data analysis and graphing are done using the TestWorks™ software.

The samples used for this test are 1" wide×4" long with the long axis of the sample cut parallel to the direction of maximum extensibility of the sample. The sample should be cut with a sharp exacto knife or some suitably sharp cutting device designed to cut a precise 1" wide sample. (If there is more than one direction of extensibility of the material, samples should be taken parallel to a representative direction of elongation). The sample should be cut so that an area representative of the symmetry of the overall pattern of the deformed region is represented. There will be cases (due to variations in either the size of the deformed portion or the relative geometries of the first and second regions) in which it will be necessary to cut either larger or smaller samples than is suggested herein. In this case, it is very important to note (along with any data reported) the size of the sample, which area of the deformed region it was taken from and preferably include a schematic of the representative area used for the sample. Three samples of a given material are tested.

The grips of the Instron consist of air actuated grips designed to concentrate the entire gripping force along a single line perpendicular to the direction of testing stress having one flat surface and an opposing face from which protrudes a half round to minimize slippage of the sample.

The distance between the lines of gripping force should be 2" as measured by a steel rule held beside the grips. This distance will be referred to from hereon as the "gauge length". The sample is mounted in the grips with its long axis perpendicular to the direction of applied percent elongation. The crosshead speed is set to 10 in/min. The crosshead elongates the sample until the sample breaks at which point the crosshead stops and returns to its original position (0% elongation).

The percent available stretch is the point at which there is an inflection in the force-elongation curve, beyond which point there is a rapid increase in the amount of force required to elongate the sample further. The average of the percent available stretch for three samples is recorded.

While the test methods described above are useful for many of the web materials of the present invention it is recognized that the test methods may have to be modified to accommodate some of the more complex web materials within the scope of the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a front waist region and a back waist region, the absorbent article comprising:
   a chassis assembly comprising a liquid pervious topsheet, a liquid impervious backsheet joined with said topsheet, and an absorbent core positioned between said topsheet and said backsheet; and
   an extensible back waist feature positioned in said back waist region, said extensible back waist feature joined to and extending longitudinally outwardly from said chassis assembly, said extensible back waist feature comprising:
   (a) a hip panel extending longitudinally outwardly from said absorbent core, said hip panel being extensible in a direction having a vector component in the lateral direction;
   (b) a central waistband panel joined to and extending longitudinally outwardly from said hip panel, said central waistband panel being extensible in a direction having a vector component in the lateral direction, the extension force of said central waistband panel being greater than the extension force of said hip panel; and
   (c) a pair of side panels joined to and extending laterally outwardly from said central waistband panel and at least a portion of said hip panel, each said side panel being extensible in a direction having a vector component in the lateral direction.

2. The absorbent article of claim 1 wherein said hip panel comprises a structural elastic-like film web comprising a strainable network of at least two contiguous, distinct and dissimilar regions, said strainable network including at least a first region and a second region having one or more rib-like elements.

3. The absorbent article of claim 2 wherein said side panels each comprise a structural elastic-like film web.

4. The absorbent article of claim 3 wherein said central waistband panel comprises a structural elastic-like film web.

5. The absorbent article of claim 4 wherein the extension force of said central waistband panel is greater than the extension force of each said side panel.

6. The absorbent article of claim 5 wherein the extension force of each said side panel is greater than the extension force of said hip panel.

7. The absorbent article of claim 6 wherein said SELF web of said central waistband panel has an extension force between about 10 g/cm and about 30 g/cm at 50% extension.

* * * * *